(12) United States Patent
Devor et al.

(10) Patent No.: US 8,106,175 B2
(45) Date of Patent: Jan. 31, 2012

(54) INTERNAL CONTROLS FOR ISOLATION OF SMALL RNAS

(75) Inventors: Eric J. Devor, Iowa City, IA (US); Lingyan Huang, Coralville, IA (US); Mark A. Behlke, Coralville, IA (US)

(73) Assignee: Integrated DNA Technologies, Inc., Skokie, IL (US)

( * ) Notice: Subject to any disclaimer, the term of this patent is extended or adjusted under 35 U.S.C. 154(b) by 0 days.

(21) Appl. No.: 12/832,567

(22) Filed: Jul. 8, 2010

(65) Prior Publication Data

US 2010/0273232 A1 Oct. 28, 2010

Related U.S. Application Data

(62) Division of application No. 12/165,436, filed on Jun. 30, 2008.

(60) Provisional application No. 60/946,922, filed on Jun. 28, 2007.

(51) Int. Cl.
*C07H 21/02* (2006.01)

(52) U.S. Cl. .................................... 536/23.1

(58) Field of Classification Search .................... None
See application file for complete search history.

(56) References Cited

U.S. PATENT DOCUMENTS 6,558,901 B1 * 5/2003 Moe et al. ..................... 435/6

OTHER PUBLICATIONS

Bartel Lab, Bartel Lab Protocol, MicroRNA and siRNA Cloning Protocol, Jul. 2005, pp. 1-8.*
Pfeffer et al., Cloning of Small RNA Molecules, Current Protocols in Molecular Biology (2003) 26.4.1-26.4.18, Supplement 64, ppp. 26.4.1-24.4.18.*
Brush, Water, Water, Everywhere: A Profile of Water Purification Systems, The Scientist 1998, 12(12):18, pp. 1-13.*
Danner et al., T7 phage display: A novel genetic selection system for cloning RNA-binding proteins from cDNA libraries, pp. 12954-12959, PNAS, Nov. 6, 2001_vol. 98_No. 23.*
Stratagene 1988 Catalog, p. 39.*
Russell et al., cDNA Cloning of the Messenger RNAs of Five Genes of Canine Distemper Virus, J. gen. Virol. (1985), 66, 433-441.*

* cited by examiner

*Primary Examiner* — Mark Staples
(74) *Attorney, Agent, or Firm* — John A. Petravich

(57) ABSTRACT

This invention pertains to methods for cloning microRNA (miRNA) and other small ribonucleic acid (RNA) species from relevant cell sources.

2 Claims, 13 Drawing Sheets

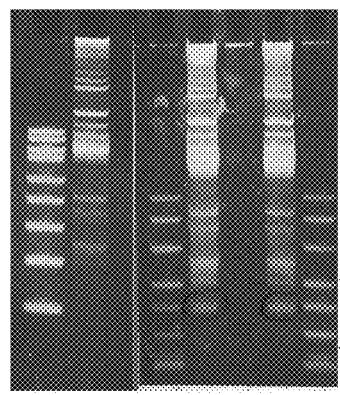
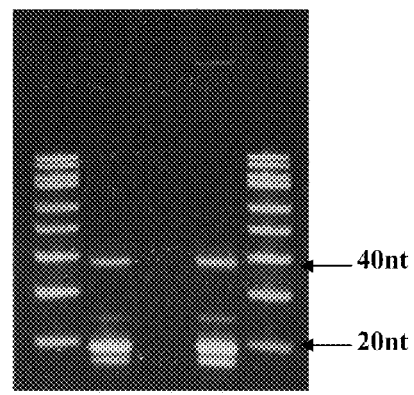
FIG. 10A
FIG. 10B
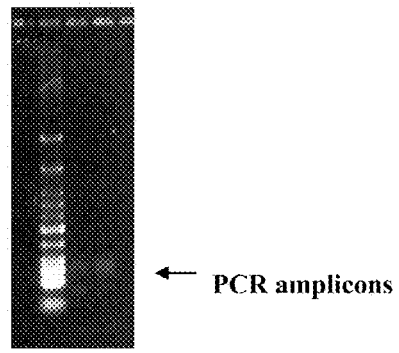
FIG. 10C

INTERNAL CONTROLS FOR ISOLATION OF SMALL RNAS

CROSS-REFERENCE TO RELATED APPLICATION

The present application is a divisional of U.S. non-provisional patent application Ser. No. 12/165,436 filed 30 Jun. 2008, which claims priority under 35 U.S.C. §119(e) to U.S. provisional application No. 60/946,922 filed 28 Jun. 2007. The entire teachings of the above application are incorporated herein by reference.

FIELD OF THE INVENTION

This invention pertains to methods for cloning microRNA (miRNA) and other small ribonucleic acid (RNA) species from relevant cell sources.

BACKGROUND OF THE INVENTION

Small, non-coding, regulatory RNA species such as microRNAs have emerged in recent years as a powerful agent in regulating gene expression in eukaryotic cells. First discovered in 1993 (Lee at al., *Cell* 75: 843-854 (1993)), microRNAs are an abundant new class of regulatory elements that have been shown to impact all aspects of normal cellular processes in both plants and animals, including cell death, differentiation, and proliferation, as well as abnormal processes including cancer (Bartel, *Cell* 116: 281-297 (2004); Du and Zamore, *Development* 132: 4645-4652 (2005); Pillai, *RNA* 11: 1753-1761 (2006)). In general, an miRNA is composed of a highly conserved core sequence of 21-23 nucleotides (the mature miRNA) contained within a less well conserved precursor sequence (pre-miRNA) ranging in size from 60 nucleotides to more than 120 nucleotides. This pre-miRNA sequence is part of a larger primary transcript that may contain a single pre-miRNA or two or more pre-miRNAs arranged as paired or polycistronic transcripts. MicroRNA expression has been found to be highly specific and, in many cases, sequestered by tissue type and/or developmental stage. For this reason, discovery of new microRNAs requires the cloning of RNA species that may be expressed only in certain cells harvested at particular times. The availability of a generally applicable and efficient cloning method is, therefore, key in advancing knowledge of both the number of microRNAs present in a given genome and their specific role in that organism's cells.

Since 2001, several methods for cloning microRNAs and other small RNA species from total cellular RNA have been advanced (Berezikov et al., 2006; Cummins et al., 2006; Elbashir et al., *Genes and Development* 15: 188-200 (2001); Lau et al., *Science* 294: 858-862 (2001); Pfeffer et al., *Current Protocols in Molecular Biology*, 26.4.1-26.4.18 (2003); Sunkar and Zhu, *The Plant Cell* 16: 2001-2019 (2004)). Cloning small RNAs generally begins with the isolation and purification of total cellular RNA from a relevant cell source. More recent variations on the basic scheme advocate enriching the RNA target pool for species in the proper size range. This entails taking the total cellular RNA pool and isolating only those RNAs that fall below or within a certain size range. Commercial products are available to remove larger RNA species from the target pool that would compete in the subsequent process that forms the substance of the described method.

Once an enhanced RNA target pool has been purified, by whatever means, the next step is to attach a 3'-end blocked linking group that will ligate to the 3'-end of the small RNA species. Generally, a 5'-end linking group is also ligated to the small RNA species. Then reverse transcriptase polymerase chain reaction (RT-PCR) is performed wherein the resulting fragments are cloned into vectors to create a cDNA library comprising a heterogeneous collection of small cellular RNA species. The cloned fragments can then be sequenced and analyzed to determine the identity and genomic origin of the small RNA species present in the sample.

Current methods have enabled investigators to identify hundreds of unique miRNAs, and there are estimates that thousands of unique miRNAs may exist. Additionally, several new classes of small, regulatory RNAs have been discovered in the past few years. These new classes include endogenous silencing RNAs (endo siRNAs), PIWI-interacting RNAs (piRNAs), 21U RNAs, and repeat-associated siRNAs (rasiRNAs), all of which have been discovered by direct cloning from specific RNA sources. Production of small RNA libraries is a complex task and it is possible to produce libraries that are incomplete or contain skewed subsets of the RNA species present in the original sample. There is a need for more efficient methods of small RNA cloning that can be used by less-skilled technicians to clone and identify miRNAs.

BRIEF SUMMARY OF THE INVENTION

The invention provides improvements to the current methods of small RNA (such as miRNA) cloning to provide greater efficiency and simplification to reduce error-rate. The invention also provides methods to monitor the quality of the reaction using an internal size marker to serve as a quality control reagent.

The method provides a synthetic RNA oligoribonucleotide that serves as an internal size marker for identifying the correct fragment sizes during RNA size purification steps needed as part of library construction. This RNA is about 21 bases in length and is a sequence that is distinct from known microRNAs. This sequence can be added to the natural RNA sample at a relatively low mass amount and initially will serve to identify the correct size range for enrichment of small RNA species as the first step of library construction. The synthetic marker sequence co-purifies along with the target RNAs and, along with the target RNAs, will participate in the 3'-linkering reactions. Ligation of a 3'-linker to the marker RNA and the target RNAs will shift the molecular weight of all species upward by the same mass amount and further will alter migration of these species on gel electrophoresis by a similar degree. Following the 3'-linkering step, the synthetic marker now serves as a size marker for isolation and enrichment of those small RNA species which have successfully been joined with the 3'-linker oligonucleotide. At this point in library construction a new 5'-linker oligonucleotide is joined to the 5'-end of the RNA species. Naturally occurring miRNAs possess a 5'-phosphate group which is needed for joining to occur if the reaction is mediated by the enzyme T4 RNA Ligase. However, the synthetic marker RNA does not contain a 5'-phosphate group which renders it inactive for the 5'-linkering step. Thus, only the target RNAs will be 5'-linkered and be available for subsequent enzymatic reactions. The presence of linker species on both the 3'-end and 5'-end of the small RNAs are required for cloning, amplification, and isolation. Therefore the synthetic RNA marker oligonucleotide serves as a marker for initial RNA isolation, serves as a positive control for 3'-linker attachment, serves as a marker for isolation of 3'-linkered species, but is blocked from further participation in the cloning process and will not be present or otherwise contaminate the final small RNA library produced by the procedure.

The invention additionally provides 5'-5'-adenylated oligonucleotides for ligation of the oligonucleotides using T4 ligase. The adenylated oligonucleotides are made by a novel chemical method by reacting 5'-monophosphate with 5'-silylated phosphate followed by oxidation by N-chlorosuccinimide (NCS) in acetonitrile. Using 5'-monophosphate instead of 5'-pyro- or 5'-polyphosphate eliminates side products because the phosphate backbone is protected by a cyanoethyl group. The adenylation reaction occurs on the support during oligonucleotide synthesis and can be isolated with a single purification. The new method of the invention does not require that adenylation be performed as an additional handling step after oligonucleotide synthesis is complete.

The invention also provides an efficient alternative to current purification practices. The original protocols for small RNA cloning required three separate denaturing polyacrylamide gel (PAGE) purification steps. Each purification step is time consuming, and each purification results in loss of product. Reducing the number of purification steps improves yield of recovered product. For this reason, small RNA cloning protocols usually require a very large mass of starting RNA. The invention eliminates one of the two PAGE purification steps generally needed to perform cloning via end linkering and therefore improves yield and permits library construction using lower input mass amounts of RNA. The methods also use a reduced amount of ligase when linking the 3'-linker to the RNA product as compared to current methods.

The method further provides improvements in the post-PCR amplification steps of the cloning process. The amplification products (amplicons) must be digested with an appropriate restriction enzyme to create the sticky ends used for concatamerization and cloning. The proposed method introduces a substantial improvement. Using conventional methods, the amplicons generated in the PCR amplification are too small to be purified by conventional means apart from excision from an agarose gel—a step that would add time, effort and expense to the protocol. Unpurified PCR reactions tend to be inefficient substrates for restriction enzyme digestion and thus purification, with loss of product, is usually performed. The proposed method utilizes phenol/chloroform/isoamyl alcohol (25:24:1) extraction followed by precipitation to enhance restriction enzyme digestion and concatamerization without additional purification. The entire cloning process for miRNA cloning with concatamerization has been abbreviated "miRCat" hereafter.

BRIEF DESCRIPTION OF THE DRAWINGS

FIG. 10A shows a photograph of a 15% denaturing PAGE gel of total RNA from *Gossipium hirsutum*, TM-1 with and without the addition of a 21-mer RNA control. Lanes 1, 3 and 7 are markers, lane 2 contains the total RNA without the 21-mer control, and lanes 4 and 6 contain the total RNA and the 21-mer control.

FIG. 10B shows a photograph of a 15% denaturing PAGE gel of the RNA fraction containing the 21-mer control (lanes 4 and 6 from the gel in FIG. 8A) post 3' linkering. The linkered material is seen as bands in lanes 2 and 3 around the 40 nt mark. Lanes 1 and 4 are marker lanes.

FIG. 10C is a photograph of a 1.4% low melting point agarose gel with the PCR amplicons from the RT-PCR. Lane 1 is a low molecular weight ladder, and lane 2 contains a band identified as "PCR amplicons" which is the recovered material from an RT-PCR reaction containing the 3' linker and the 5' 454 sequence.

DETAILED DESCRIPTION OF THE INVENTION

Figure 1:
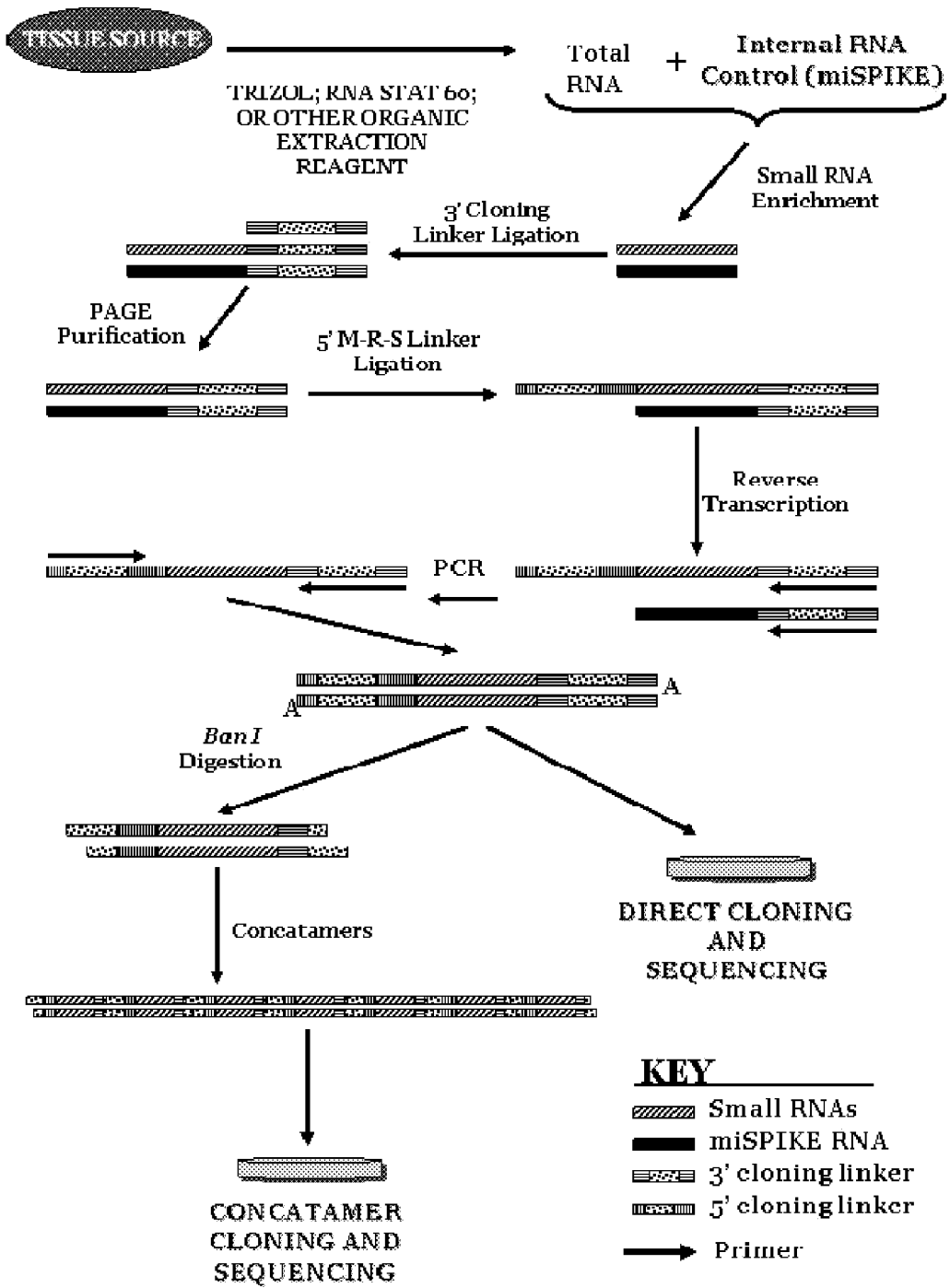
FIG. 1 is an illustration of a complete process of cloning small RNAs from a tissue or cell source using the described methods.

The invention provides improvements to the current methods of cloning small RNA species to provide greater efficiency and simplification to reduce errors and increase yields. The invention also provides methods to monitor the quality of the reaction using a quality control reagent. FIG. 1 illustrates the complete cloning process of one embodiment of the proposed invention.

Figure 2:
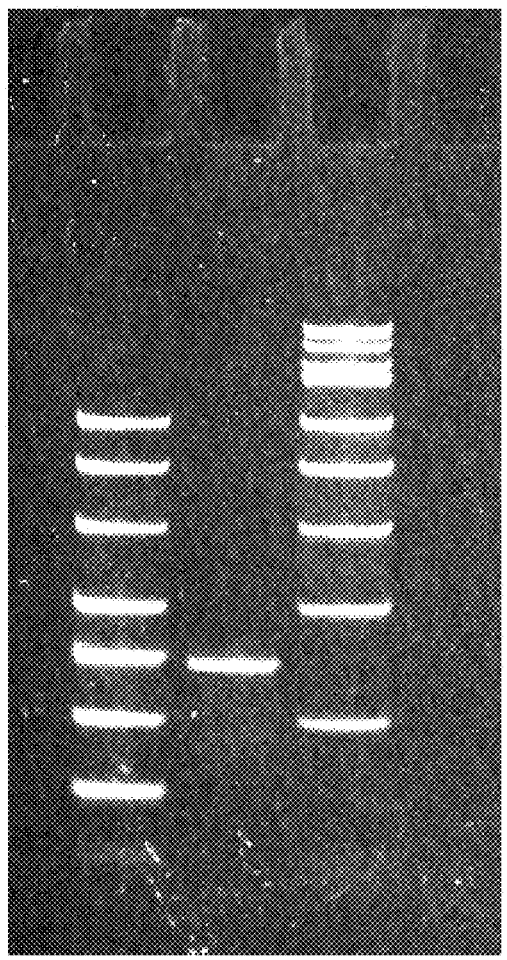
FIG. 2 is a picture of a gel containing an RNA sample stained with a nucleic acid stain. Lanes 1 and 3 contain single-stranded DNA ladders, and Lane 2 contains single-stranded RNA.

The invention provides a non-radioactive staining method to identify materials, wherein the staining does not affect downstream applications. Because of the small amount of small RNA species present in a typical sample, conventional methods generally utilize radiolabeled markers to help isolate the small RNA species. The present method utilizes a simple nucleic acid gel stain, such as Gelstar® (Lonza®). As demonstrated in FIG. 2, the stain provides clear bands, and the stain does not have any noticeable effect on downstream applications (e.g., enzyme reactions, ligations, and the like).

The method also provides a synthetic oligoribonucleotide (ORN) that will serve as an internal size marker for identifying the correct fragment sizes during RNA size purification. The ORN is about 19-23 bases in length and is a sequence that is distinct from known microRNAs. Preferably, the ORN is about 20-22 bases in length and is a sequence that is distinct from known microRNAs. More preferably, the ORN is 21 bases in length and is a sequence that is distinct from known microRNAs. Small mass amounts of this ORN are added into the RNA sample that is being used for cloning as a size/mass marker to identify the correct size range for enrichment of the RNA pool during purification steps. The RNA sample is then subjected to purification. Any of a number of methods can be employed. PAGE purification is most commonly performed. The ORN marker co-purifies with the target RNAs and, like the natural small RNA species present, will participate in the subsequent 3' linkering step wherein it then serves as a marker for collecting the linkered RNAs as well as a positive control for the 3'-linker step. The ORN marker does not contain a 5' phosphate group which renders it inactive for the 5' linkering step. Thus, only the target RNAs will be 5' linkered and be available for downstream procedures.

Similar synthetic ORN markers can be devised for other classes of target RNAs that may vary in size. For example, a synthetic ORN marker of about 30-31 nucleotides long could be constructed to serve as a control for the isolation and cloning of piwi-interacting RNAs (piRNAs), which are typically 26-32 nucleotides long.

In one embodiment, the synthetic ORN marker is comprised of a sequence that is not a recognized miRNA or other naturally occurring sequence. The marker's sequence can be verified against established miRNA sequence databases to ensure that there is no match between the marker and any known miRNAs. One such sequence is described below. It will be appreciated by one skilled in the art that need may arise to adjust or change the sequence of the synthetic ORN marker as new miRNA species are discovered which, by happenstance, may have similar or identical sequence to the exemplary sequence employed herein.

In another embodiment, the RNA construct is the following sequence.

```
                                        SEQ ID NO: 1
5'-rCrUrCrArGrGrArUrGrGrCrGrGrArGrCrGrGrUrCrU-3'
```

The sequence has been checked through miRNA databases GenBank and miRBase (via BLAST) resulting in no match to any known species. When SEQ ID NO:1 is added to a sample, the resulting library is of higher quality than that obtained without SEQ ID NO:1. As expected, the resulting clones within the library did not contain the RNA construct, which may indicate that the synthetic ORN marker acts as a carrier or provides some mechanism to offer a synergistic effect for the cloning of the sample.

Figure 3A:
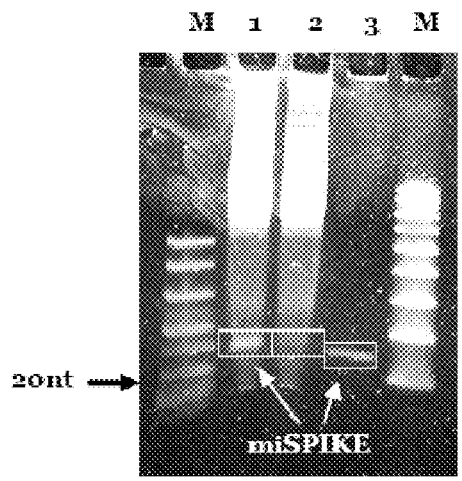
FIG. 3A is a 12% 7M urea PAGE (275 v, 90 min) gel showing small RNA enrichment from total cellular RNA. Lanes 1 and 2 contain 50 µg of cellular RNA. Lane 1 contains 10 pmole of SEQ ID NO:1 but Lane 2 does not. Lane 3 is 10 pmole of SEQ ID NO:1 only. The boxes indicate the gel slices taken for small RNA purification.

As illustrated in FIG. 3A, when 10 pmole of SEQ ID NO:1 ("miSPIKE") are added to 50 μg of cellular RNA, an easily identifiable band is visible in the gel region corresponding to desired RNA length. Lane 1 contains both SEQ ID NO:1 and the cellular RNA, lane 2 contains only cellular RNA and lane 3 contains only SEQ ID NO:1. The SEQ ID NO:1 sample is visible in lanes 1 and 3.

Figure 3B:
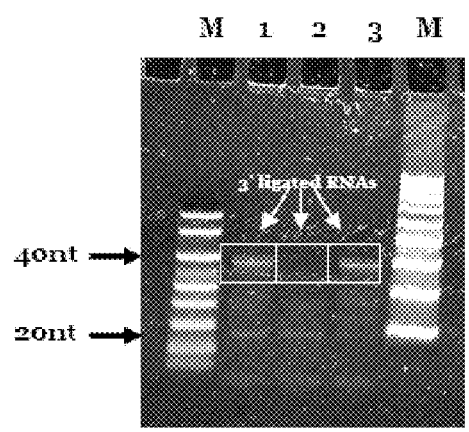
FIG. 3B is a 12% 7M urea PAGE (275 v, 90 min) gel showing recovery of 3' ligated RNAs from the sample in FIG. 3A. Lane 1 contains 10 pmole of SEQ ID NO:1 but Lane 2 did not. Lane 3 is 10 pmole of SEQ ID NO:1 only. The boxes indicate the gel slices taken for small RNA purification in preparation for further ligations.
Figure 3C:
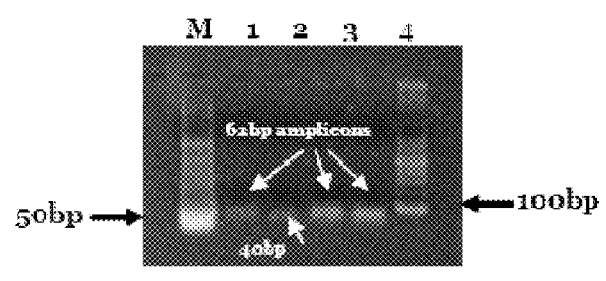
FIG. 3C is a 1.3% low melting point agarose gel showing PCR amplification of doubly-ligated RNAs from the sample in FIG. 3B. Lane 1 is a conventional 3' plus 5' miRCat ligation. Lane 2 is ligation with only SEQ ID NO:1. Lane 3 is a 5' ligation-independent (miRCat-33) cloning lane from RNA not containing SEQ ID NO:1. Lane 4 is a SEQ ID NO:1 only 5'-LIC showing that SEQ ID NO:1 will clone using 5'-LIC whereas Lane 2 shows that SEQ ID NO:1 will not clone using the conventional miRCat method.

FIG. 3B shows a gel containing the corresponding samples from FIG. 3A after the 3' ligation step. Again, lanes 1 and 3 are visible due to the presence of SEQ ID NO:1. And FIG. 3C shows PCR amplification of doubly-ligated RNAs. Lane 1 is a conventional 3' plus 5' miRCat ligation. Lane 2 is a miSPIKE only ligation. Lane 3 is a 5' ligation-independent (miRCat-33) cloning lane from RNA not containing miSPIKE. Lane 4 is a miSPIKE only 5'-LIC showing that miSPIKE will clone using 5'-LIC whereas Lane 2 shows that miSPIKE will not clone using the conventional miRCat only method.

A second embodiment is the following sequence.

```
                                        SEQ ID NO: 2
    5'-rCrUrCrArGrGrArUrGrGrCrGrGrArGrCrGrG
       rGrUrCrUrCrArCrUrGrArArCrGrU-3'
```

The sequence, which is a ten base extension of SEQ ID NO:1, has also been checked through databases GenBank and miRBase (via BLAST) resulting in no match to any known small RNA species.

The invention also provides an efficient alternative to current purification practices. The original protocols for small RNA cloning required three separate denaturing polyacrylamide gel (PAGE) purification steps. Each of these is time consuming and each has an associated cost in terms of lost mass. The purification method associated with PAGE causes an unavoidable loss of material regardless of how carefully the procedure is carried out. For this reason, the early protocols required a very large mass of starting RNA. The invention eliminates one of the three PAGE purifications and its attendant loss of material. In addition, the invention also provides an alternative purification method for the remaining two PAGE purifications that reduce both time and material loss. The alternative uses a dye-terminator removal cartridge (DTR, Edge Biosystems) to remove salts and urea from an acrylamide gel slice. The methods also use a reduced amount of ligase when linking the 3' linker to the RNA product as compared to current methods.

Similarly, a variety of different sequences could be used to direct RT-PCR of the linkered small RNA species, so long as they are sufficiently complementary to anneal to the 5'- and 3'-linkers in conditions employed in PCR. A first embodiment consists of unmodified DNA oligonucleotides that are used for reverse transcription and for PCR amplification of the RT products for direct cloning (SEQ ID NO:3 and SEQ ID NO: 4).

```
5'-GATTGATGGTGCCTACAG-3'     SEQ ID NO: 3

5'-TGGAATTCTGGGCACC-3'       SEQ ID NO: 4
```

A second embodiment consists of DNA oligonucleotides each modified with a 5' biotin for use in concatamer construction methods from PCR amplicons as a variant to direct cloning (SEQ ID NO: 5 and SEQ ID NO: 6). The Reverse Transcription step is still performed using an unmodified primer (SEQ ID NO:3) when later performing PCR amplification using biotin-modified primers.

```
5'-Biotin-GATTGATGGTGCCTACAG-3'     SEQ ID NO: 5

5'-Biotin-TGGAATTCTGGGCACC-3'       SEQ ID NO: 6
```

A third embodiment combines the two functions into a single pair of modified DNA oligonucleotides that can be used for either approach. The sequences contain a biotin-dT as the penultimate 5' nucleotide and an additional unmodified nucleotide at the 5' end, thereby making the biotin-dT an internal biotin label (SEQ ID NO: 7 and SEQ ID NO: 8).

```
5'-C-Biotin dT-GATTGATGGTGCCTACAG-3'    SEQ ID NO: 7

5'-C-Biotin dT-TGGAATTCTGGGCACC-3'      SEQ ID NO: 8
```

The internal biotin-dT does not interfere with either the Reverse Transcription reaction or with PCR amplification. Thus, the RT step and both of the PCR amplification/cloning options can be carried out with the same two modified oligonucleotides. The use of the internal biotin-dT allows for PCR amplification with or without restriction enzyme (in this case, Ban I) digestion and magnetic bead removal of the fragment ends. Therefore PCR products generated with these two primers can either be cloned directly or concatamerized.

An alternative concatamerization method that does not require biotinylated oligonucleotides can be substituted that lowers cost without grossly affecting results.

The invention additionally provides a 5'-5'-adenylated oligonucleotides for ligation of the oligonucleotides to a target RNA species using T4 RNA Ligase. (SEQ ID NO: 9). This oligonucleotide also contains a 3' dideoxycytidine base to prevent reactions on that end.

```
5'-rAppCTGTAGGCACCATCAAT/3ddC/-3'    SEQ ID NO: 9
```

It will be appreciated by one skilled in the art that a large number of different sequences could perform well as the synthetic adaptor oligonucleotide employed in the 3'-linkering step. It is, however, crucial that these sequences contain 1) an activated adenylyl group at the 5'-end that permits ligation using T4 RNA Ligase in the absence of ATP, 2) internal restriction endonuclease sites suitable for use in library cloning, and 3) a blocked 3'-end that cannot participate in ligation reactions.

The adenylated oligonucleotides are made using a novel chemical method that is more direct and simple than traditional chemical adenylation methods by reacting 5'-monophosphate with 5'-silylated phosphate followed by oxidation by N-chlorosuccinimide (NCS) in acetonitrile. Using 5'-monophosphate instead of 5'-pyro- or 5'-polyphosphate eliminates side products because the phosphate backbone is protected by a cyanoethyl group. The adenylation occurs on the support and can be purified in a single step. No post-synthetic chemical reactions are necessary. All steps can be performed "on column" on a nucleic acid synthesis machine.

The methods further provide post-PCR amplification improvements. The amplification products (amplicons) must be digested with the appropriate restriction enzyme to create the sticky ends used for concatamerization and subsequent cloning. The proposed method introduces a substantial improvement. Using conventional methods, the amplicons generated in the PCR amplification are too small to be purified by conventional means apart from excision from an agarose gel—a step that would add time, effort and expense to the protocol. Unpurified PCR reactions tend to perform less well than purified PCR products for restriction enzyme digestion. The proposed method utilizes a commercial Dye Terminator Removal (DTR) spin cartridge (Edge BioSystems) to clean up DNA sequencing reactions, having a salutary effect on restriction enzyme digests of small amplicon residual primers and salts from the PCR reactions resulting in products that function with high efficiency in restriction enzyme digestions. Moreover, there is virtually no loss of reaction mass during the clean-up.

The following examples further illustrate the invention but, of course, should not be construed as in any way limiting its scope.

Example 1

This example provides a protocol for practicing the proposed microRNA cloning process. Total RNA is prepared using methods well-known in the art, such as the use of the MIRVANA™ RNA isolation kit (Ambion®) following the Ambion® protocol. RNA isolation methods utilizing glass fiber filters (GFF) or silicate adsorption should be avoided as these "rapid" methods for RNA isolation often deplete the small RNA pool present in a natural sample. Organic extraction reagents such as Trizol or RNA STAT 60 are preferred. After the RNA is extracted and purified, the sample is enriched for small RNA species. If practical, it is preferred to employ at least 50 µg to 100 µg of total RNAs for small RNA enrichment however lower input mass amounts can be used when sample is limited. The mass of RNAs in the miRNA size range of 18 nt to 26 nt is a very small fraction of the total RNA present, and size selection at this stage of library construction is essential to the quality of the end product. The conventional means of purifying small RNA fractions is through the use of a 12% denaturing (7M Urea) polyacrylamide gel (denaturing PAGE).

Figure 4:
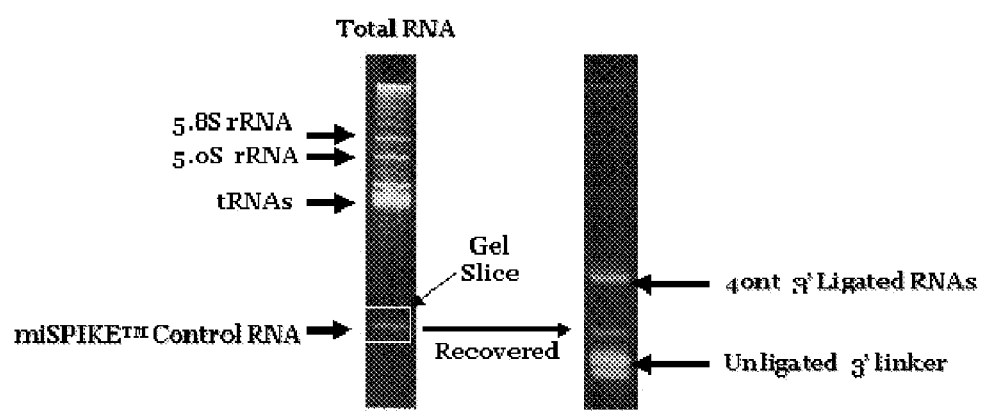
FIG. 4 is an example of the two PAGE RNA purification gels. On the left is the 12% denaturing PAGE containing total RNA spiked with the 21-mer control RNA. On the right is the second 12% denaturing PAGE in which the spiked RNA recovered from the gel slice is 3' ligated. Material at the 40 nt size is recovered and purified for the subsequent 5' linkering step.

Internal control oligonucleotide. 10 pmol (1 µl) of the internal ORN Marker was added to the total RNA before loading the acrylamide gel. Following electrophoresis, the gel was stained with GelStar® Nucleic Acid Stain, and the 21-mer ORN Marker is clearly visualized. FIG. 4 provides an example of a gel prepared in this fashion. To obtain an enriched small RNA fraction, the gel is cut 2 mm above and below the control marker band and the small RNA species are eluted from the excised gel slice.

The RNA is recovered using a standard crush and soak recovery method. The gel slice(s) is placed in a tube such as a 1.5 ml RNase-free tube and, using an RNase-free glass rod, the gel slice is crushed. An equal volume of nuclease-free water is added to the tube (the gel slice is weighed to determine this volume at 1 ml/g). The suspension is vortexed for 15-30 seconds, then heated to 70° C. for 10 minutes, and then optionally vortexed again for 15-30 seconds. A Performa® spin column (Edge Biosystems) is prepared for each gel slice by centrifuging the column at 3,000 rpm for 3 minutes. The column is then transferred to a receiving tube. The vortexed slurry is transferred to a spin column and spun at 3,000 rpm for 3 minutes. 3 µl 10 mg/ml glycogen, 25 µl of 3M NaOAc (pH 5.2) and 900 µl ice cold 100% EtOH is added to the eluent. The solution is mixed by inversion and then placed at −80° C. for 20 minutes. The tubes were centrifuged at 16,000×g for 10 minutes. The supernatant was drained off and the pellet was dried.

Alternatively, the RNA can be recovered from the denaturing PAGE using DTR columns (Edge Biosystems DTR Gel Filtration Cartridges Cat. No. 42453). This protocol successfully removes the urea and other salts with substantially less loss of RNA than is seen with conventional crush and soaks methods followed by NAP-5 column desalting. The total RNA was size separated on a 15% denaturing PAGE (7M Urea) for 90 minutes at 275V and then the gel was stained with GelStar® nucleic acid stain (Lonza®) and placed on a long wavelength (312 nm) UV light box. Next, the RNA fragment(s) to be purified are excised from the gel and placed in a 1.5 ml tube and crushed with a glass rod. 200 µl sterile, nuclease-free water is added while continuing to crush the gel into a slurry. The tube is placed at 70° C. for 10 minutes. Following manufacturer's recommendations, prepare a DTR column (EDGE Biosystems®) for each gel slice and vortex the gel slice slurry and transfer the entire volume onto the DTR column and spin at 850×g for 3 minutes. Next, discard the DTR column and add 3 µl 10 mg/ml glycogen, 25 µl of 3 M NaOAc (pH 5.2), and 900 µl ice cold 100% EtOH. Mix by inversion and hold at −80° C. for 30 minutes. Spin the tubes at 16,000×g for 10 minutes, pour off the supernatant and dry the RNA.

Other methods are available to select for small RNA species. One option is the MIRVANA™ miRNA Isolation Kit (Ambion®, Cat. No. AM1560) that uses spin columns for selecting RNA less than 200 nt in length. The other is the flashPAGE™ fractionator (Cat. No. AM13100) that electrophoretically excludes RNA species greater than 40 nt in length.

RNA linkering. Once the enriched small RNA fraction has been recovered from the acrylamide gel slice, the small RNAs are ligated with a 3' and a 5' linker in two separate, sequential reactions. The first reaction is the 3' ligation. In order to avoid circularization of the RNA fragments, the 3' linker is ligated to the small RNAs using T4 RNA ligase in the absence of ATP. This reaction requires use of a pre-activated 5' adenylated (rApp) cloning linker with a 3' ddC end-block (Lau et al., 2001).

In an RNase-free 0.2 ml tube the following are added:

| | |
|---|---|
| Recovered small RNA fraction | y µl |
| 3' RNA linker (50 µM) | 1 µl |
| 10X Ligation Buffer | 2 µl |
| Ligation Enhancer (such as DMSO) | 6 µl |
| T4 RNA Ligase (1 U/µl) | 1 µl |
| IDT water | (10 − y) µl |
| Total Volume | 20 µl |

The 10× Ligation Buffer is a reaction buffer. SEQ ID NO:9 is an example of a 3' linker that has been utilized in cloning. The Ban I restriction endonuclease site is underlined.

```
5'-rAppCTGTAGGCACCATCAAT/3ddC/-3'   SEQ ID NO: 9
```

The above reagents are incubated at 22° C. for two hours. Then 80 µl IDTE (pH 7.5) is added and the entire volume is transferred to an RNase-free 1.5 ml tube. 3 µl glycogen (10 mg/ml), 1/10 volume (10 µl) 3.0 M NaOAc and 2.5 volumes (250 µl) −20° C. 100% EtOH are added. The sample is mixed by inversion or vortexed briefly, and then placed at −80° C. for 30 min. The sample is centrifuged at 16000×g for 10 min. The supernatant is removed, and the pellet is dried completely and resuspended in 10 µl DNase/RNase/pyrogen-free water.

Page purification of 3'-linkered products. Any free 3'-linker present will compete with the linkered small RNAs for ligation in the subsequent 5' ligation step. Unreacted linkers are therefore removed by PAGE purification. Ligated RNAs are 40 nt long while the unligated 3' linker is 19 nt long. These sizes are easily resolved on a 12% denaturing (7M urea) polyacrylamide gel (see FIG. 4). The linkered RNAs are recovered using the same methods as employed during the enriched small RNA enrichment process performed earlier. The gel is stained with GelStar® and cut out 2 mm above and below the 40 nt band. The RNA is recovered using the spin columns.

5' Linkering reaction. The 5' multiple restriction site (M.R.S.) linker is ligated to the 3' linkered small RNAs in the presence of 1.0 mM ATP. The M.R.S. contains five restriction sites and is therefore compatible with many cloning vectors. Several different 3' linkers can be utilized with this single 5'-linker. The Ban I 3'-linker employed herein is similar to the "modban" sequence employed by Lau and Bartel (Lau et al., Science, 294:858-62, 2001) and contains a Ban-I restriction site. We have also performed the same cloning process using a second 3'-linker that contains Ava-I and Sty-I restriction sites. We have also performed the same cloning process using a third 3'-linker that contains Eco RI and Msp-I restriction sites which was adapted from Pfeffer and Tuschl (Pfeffer et al., Nat Methods, 2, 269-276, 2005). All three linkers are modified with a 3'-terminal dideoxy-C (ddC) base to prevent self ligation. Other methods to block the 3'-end could be used and are well known in the art. The following sequence is the M.R.S. linker employed in the present example. It will be appreciated that many different 5'-linker sequences could be employed, so long as the restriction sites present are compatible with the restriction sites present in the 3'-linker and the intended cloning vector. It is preferred that 6 bases or more from the 3'-end of this linker be RNA bases. It is more preferred that 10 bases or more at the 3'-end of this linker be RNA bases. It is even more preferred that 15 bases or more at the 3'-end of this linker be RNA bases. RNA content at the 3'-end of the 5'-linker improves reaction efficiency with T4 RNA Ligase.

```
                                            SEQ ID NO: 10
5' TGGAATrUrCrUrCrGrGrGrCrArCrCrArArGrGrU 3'
```

The following are added to an RNase-free 0.2 ml tube:

| | |
|---|---|
| Recovered 3' linkered RNA fraction | y µl |
| 5' RNA linker (50 µM) | 1 µl |
| 10X Ligation Buffer | 2 µl |

| | |
|---|---|
| Ligation Enhancer | 6 μl |
| 10 mM ATP | 2 μl |
| T4 RNA Ligase (5 U/μl) | 1 μl |
| RNase/DNase/pyrogen-free water | (8 − y) μl |
| Total Volume | 20 μl |

The ligation reactions are incubated at 22° C. for two hours.

Following incubation, 80 μl IDTE (pH 7.5) is added and the entire volume is transferred to an RNase-free 1.5 ml tube. 3 μl glycogen (10 mg/ml), 1/10 volume (10 μl) 3.0 M NaOAc and 2.5 volumes (250 μl)−20° C. 100% EtOH is then added. The sample is mixed by inversion or vortexed briefly and then placed at −80° C. for 30 min. The sample is then centrifuged at 16000×g for 10 min. and the supernatant is removed. The pellet is completely dried and resuspended in 10 μl nuclease/pyrogen-free water. It is not necessary to gel purify this reaction. If it is purified, it should be performed using the same protocol as was employed previously.

Reverse Transcription. The 5' and 3' ligated RNAs contain both RNA and DNA domains. These are converted to DNA via reverse transcription using a RT/REV primer. For this example, the cDNA reverse transcripts have Ban I restriction sites at both ends that were designed into the linkers. The following protocol uses SuperScript™ III Reverse Transcriptase (Invitrogen, Carslbad, Calif.; Cat. Nos. 18080-093 or 18080-044).

The following was added to an RNase-free 0.2 ml tube:

| | |
|---|---|
| Recovered linkered RNA fraction | y μl |
| dNTPs (10 mM) | 1.0 μl |
| RT primer (10 μM) | 1.0 μl |
| DNase/RNase/pyrogen-free water | (11.0 − y) μl |
| Total Volume | 13.0 μl |

The sample was incubated at 65° C. for 5 minutes, placed on ice, and then 4 μl 5× First Strand Buffer, 1 μl 0.1 M DTT, 1 μl RNase-OUT™ (40 U/μl), and 1 μl SuperScript™ III RT (200 U/μl) 1 μl were added for a total volume of 20 μl. The sample was incubated at 50° C. for one hour followed by a 15 minute incubation at 70° C.

PCR amplification, restriction endonuclease digestion and concatamerization/cloning. The double-stranded DNA products that result from above can be directly cloned as single inserts into a plasmid vector or can be serially contatamerized so that multiple species will clone into each plasmid. Direct cloning is simpler and is preferred for use in sequencing methods that result in short read lengths (<100 bases). Concatamer cloning results in long inserts that are more efficient for use in sequencing methods that result in long read lengths (>300 bases).

For concatamerization/cloning, a previously optimized SAGE protocol coupled with concatamerization protocols from the laboratories of Dr. David Bartel (Lau et al., *Science* 294: 858-862, 2001), Dr. Andrew Fire (Pak and Fire, *Science* 315: 241-244, 2007), and Dr. Victor Velcelescu (Cummins et al., *PNAS* 103: 3687-3692, 2006) can be used. Concatamerization requires significantly more amplicon mass than is routinely obtained in a single PCR amplification. Therefore, six parallel PCR amplification reactions in separate nuclease-free 0.2 ml tubes are assembled as follows:

| | |
|---|---|
| Reverse transcription reaction | 3.0 μl |
| DNase/RNase/pyrogen-free water | 35.5 μl |
| 10X PCR Buffer | 5.0 μl |
| MgCl$_2$ (1.5 mM) | 3.0 μl |
| dNTPs (10 mM) | 1.0 μl |
| Forward Primer (10 μM) | 1.0 μl |
| Reverse Primer (10 μM) | 1.0 μl |
| Taq polymerase (5 U/μl) | 0.5 μl |
| Total Volume | 50.0 μl |

The PCR conditions are: 95° C. for 5 minutes; 25 cycles of 95° C. for 30 seconds, 52° C. for 30 seconds and 72° C. for 30 seconds; and finally 72° C. for 5 minutes. SEQ ID NO:4 is the PCR forward primer and SEQ ID NO:3 is the reverse primer.

5'-TGGAATTCTCGGGCACC-3'  Tm = 55.0° C.  SEQ ID NO: 4

5'-GATTGATGGTGCCTACAG-3'  Tm = 50.2° C.  SEQ ID NO: 3

The quality of the PCR amplification can be evaluated by running 5 μl of each reaction on a high percentage agarose gel. The expected amplicon size is 62 bp. The remaining 45 μl of each of these reactions are pooled in a single 1.5 ml tube.

For amplicon processing, an equal volume (270 μl) is added of phenol:chloroform:isoamyl alcohol (25:24:1) to the 1.5 ml tube, vortexed and then centrifuged at 16000×g for 5 min. The upper (aqueous) phase is transferred to a new 1.5 ml tube and 1/10 volume (27 μl) of 3 M NaOAc (pH 5.2) and three volumes (900 μl) of cold 100% EtOH are added. The tube is placed at −80° C. for 20 minutes, centrifuged at 16000×g for 10 minutes and the supernatant is removed. The pellet is washed in 900 μl of ice cold 70% EtOH and centrifuged again at 16000×g for 10 minutes. The supernatant is removed and the pellet is dried. Then 20 μl of DNase/RNase/pyrogen-free water is added.

The concentrated amplicon pool is digested with Ban I restriction endonuclease (New England Biolabs R0118S) for 1 hour at 37° C. with the following reagents:

| | |
|---|---|
| Amplicon Pool | 20 μl |
| 10X Ban I Buffer | 3 μl |
| DNase/RNase/pyrogen-free water | 5 μl |
| Ban I (20 U/μl) endonuclease | 2 μl |
| Total Volume | 30 μl |

Following digestion, 30 μl of phenol: chloroform: isoamyl alcohol (25:24:1) is added and the sample is vortexed and centrifuged at 16000×g for 3 minutes. The upper (aqueous) phase is transferred to a new tube and 3 μl of 3 M NaOAc (pH 5.2) and 100 μl of ice cold 100% EtOH are added. The tube is placed at −80° C. for 20 minutes, centrifuged again at ~16000×g for 10 minutes, and the supernatant is removed. The pellet is washed in 100 μl of ice cold 70% EtOH. The sample is centrifuged again at 16000×g for 10 minutes, the supernatant is removed the pellet is dried. 7 μl nuclease/pyrogen-free water is added.

For concatamerization, the following reagents are added:

| | |
|---|---|
| Ban I digested amplicons | 15 μl |
| 10X Ligation Buffer | 2 μl |

-continued

| 10 mM ATP | 2 µl |
|---|---|
| T4 DNA Ligase (30 U/µl) | 1 µl |
| Total Volume | 20 µl |

This reaction is incubated overnight at room temperature.

To prepare the concatamers for cloning into a PCR cloning vector it is necessary to fill in the 3' concatamer ends and to add an overhanging adenosine nucleotide. The following reagents are added to the 20 µl concatamer reaction:

| 10 mM dNTPs | 1.7 µl |
|---|---|
| MgCl$_2$ | 2.4 µl |
| 10X PCR Buffer | 3.0 µl |
| DNase/RNase/pyrogen-free water | 2.4 µl |
| Taq polymerase (5 U/µl) | 0.5 µl |
| Total Volume | 30 µl |

This reaction is incubated at 95° C. for five minutes, 72° C. for ten minutes, and then cooled to 25° C. before cloning. The reaction can be passed through a QIAQuick® PCR clean up column (QIAGEN Cat. No. 28104) to remove buffers and dNTPs. This is also desirable as there will be small, unligated fragments that can possibly compete in the cloning reaction. The QIAQuick® column removes a significant amount of these smaller, competing fragments.

Cloning. Cloning can be performed using a standard PCR cloning vector such as TOPO TA Cloning® (Invitrogen) or pGEM® T-EASY (Promega). Cloning should proceed according to the protocol supplied with the vector.

Concatamers result in a series of small RNAs separated by well defined linker units in which the Ban I restriction endonuclease site is reconstituted. The connector sequence is SEQ ID NO:11 or it can be SEQ ID NO:12 if the concatamers are inserted in the reverse orientation.

```
CTGTAGGCACCAAGGT     SEQ ID NO: 11

ACCTTGGTGCCTACAG     SEQ ID NO: 12
```

Figure 5:
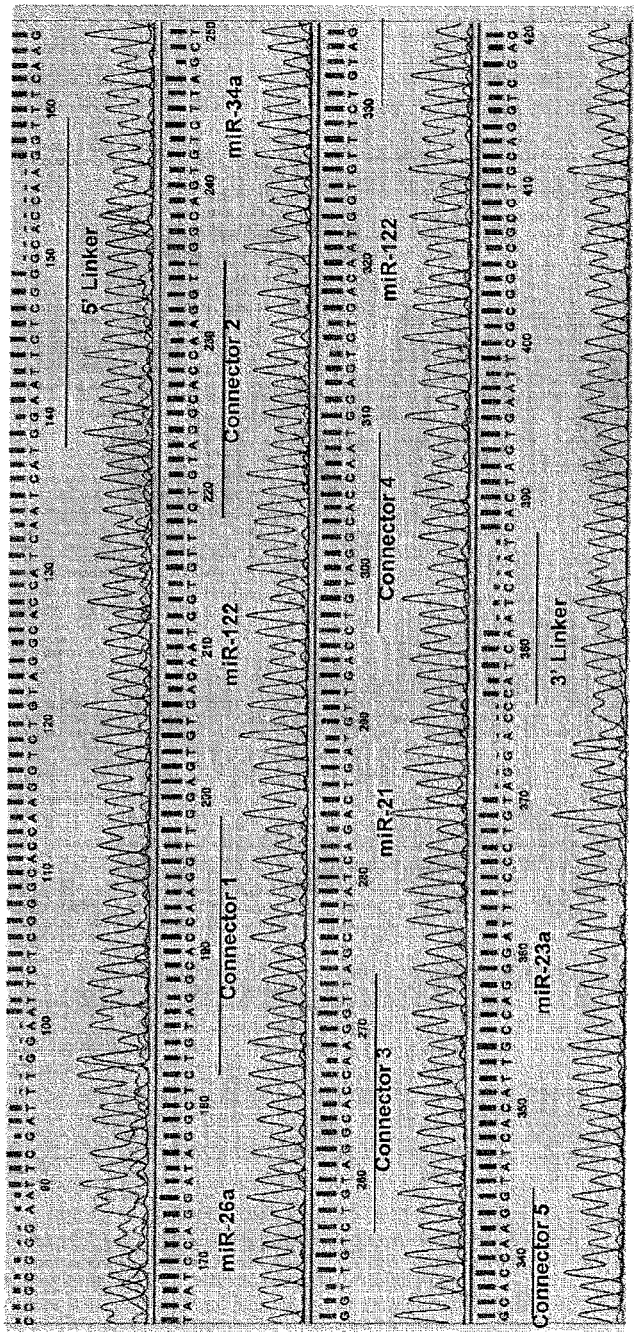
FIG. 5 is an electropherogram of a microRNA concatamer sequence containing six microRNAs. The 5' linker is at position 138-159 followed by miR-26a; Connector 1 is at 182-198 followed by miR-122a; Connector 2 is at 219-235 followed by miR-34a; Connector 5 is at 258-274 followed by miR-21; Connector 4 is at 297-308 followed by miR-122a; Connector 5 is at 330-346 followed by miR-23a; and the 3' linker is at 368-385.

These connector sequences are not always perfectly reconstituted so some care needs to be taken in reading the sequence traces. FIG. 5 illustrates an electropherogram of a microRNA concatamer sequence containing six microRNAs. The 5' linker is at position 138-159 followed by miR-26a; Connector 1 is at 182-198 followed by miR-122a; Connector 2 is at 219-235 followed by miR-34a; Connector 3 is at 258-274 followed by miR-21; Connector 4 is at 297-308 followed by miR-122a; Connector 5 is at 330-346 followed by miR-23a; and the 3' linker is at 368-385. Note that four of the five connectors are canonical but that connector four is truncated. Connectors 1-3 and 5 are SEQ ID NO: 11, and Connector 4 is the same as SEQ ID NO:11 except the last three bases on the 3' end (GGT) are missing.

A second option for cloning is to clone the PCR amplicons from the reverse transcription directly using a standard PCR cloning vector such as TOPO TA Cloning® (Invitrogen) or pGEM® T-EASY (Promega). Cloning proceeds according to the protocol supplied with the vector. While this option is less efficient than the SAGE-like concatamerization method for sequencing, it does not require the additional steps needed for the latter.

Example 2

The following example demonstrates the use of the method of the invention to isolate novel miRNAs from tissue.

Total RNA was prepared from brain, heart, lung, liver and kidney tissue of the South American marsupial species *Monodelphis domestica* using the MIRVANA™ RNA isolation kit (Ambion®, Austin, Tex.) according to the manufacturer's protocol. Between 100 µg and 200 µg of total cellular RNA was obtained from each tissue fragment. A 100 µg RNA pool, comprising 20 µg of RNA from each tissue, was used as the RNA source for the experiment. This pooled RNA sample was spiked with 10 pmole of the 21 nt internal control ORN marker "miSPIKE" and size fractionated on a 12% denaturing (7M urea) polyacrylamide gel at 275 volts for 90 minutes.

```
                                              SEQ ID NO. 1
5'-rCrUrCrArGrGrArUrGrGrCrGrGrArGrCrGrGrUrCrU-3'
```

The gel was stained with GelStar® and RNAs were visualized under UV excitation. A 4 mm square gel slice was excised using the miSPIKE ORN marker as a size guide. The gel slice was cut 2 mm above the ORN marker and 2 mm below the marker, thereby recovering RNAs in ~19-24 nt size range. The gel slice was pulverized in 200 µl of sterile, RNase-free water in a 1.5 ml microcentrifuge tube. The pulverized slurry was heated at 70° C. for 10 minutes and the entire volume was loaded on an EDGE Biosystems Performa® spin column and centrifuged for 3 minutes at 3,000 rpm. The target RNAs passed through the column and were recovered in the eluent while the acrylamide, salts and urea were retained within the column. The RNAs were precipitated with the addition of 3 µl of 10 mg/ml glycogen, 25 µl of 3M sodium acetate (pH 5.2), and 900 µl of cold 100% ethanol. The precipitated RNA was centrifuged for 10 minutes at 13,500 rpm to pellet the RNAs and was dried under vacuum.

3' small RNA linkering. The target RNAs were ligated to the adenylated 3' cloning linker Ban I (Linker 1 and SEQ ID NO:3) using the protocol in Example 1. In order to avoid circularization of the small RNAs, the 3' linker is ligated to the small RNAs using T4 RNA Ligase in the absence of ATP. This reaction involves a pre-activated 5' adenylated (rApp) cloning linker with a 3' ddC end-block (Lau et al., 2001).

In an RNase-free 0.2 ml tube the following reagents were added:

| Recovered small RNA fraction | 6 µl |
|---|---|
| 3' RNA linker (50 µM) | 1 µl |
| 10X Ligation Buffer | 2 µl |
| DMSO | 6 µl |
| T4 RNA Ligase (1 U/µl) | 1 µl |
| Nuclease-free water | 4 µl |
| Total Volume | 20 µl |

The 10x Ligation Buffer employed was the buffer provided by Epicentre Technologies with their T4 RNA Ligase. In this case, DMSO serves as a ligation enhancer which improves efficiency of the reaction. SEQ ID NO:3 is an adenylated cloning linker containing a Ban I restriction endonuclease site, which is underlined.

```
5'-rAppCTGTAGGCACCATCAAT/3ddC/-3'    SEQ ID NO: 9
```

The ligation reaction was incubated at 22° C. for two hours. Then 80 µl TE (pH 7.5) was added and the entire volume transferred to an RNase-free 1.5 ml tube. 3 µl glycogen (10 mg/ml), 1/10 volume (10 µl) 3.0 M NaOAc and 2.5 volumes (250 µl) 100% EtOH were added, mixed, then placed at −80°

C. for 30 min. The sample was centrifuged at 16000×g for 10 min. The supernatant was removed, the pellet was dried and resuspended in 10 µl water.

Figure 6:
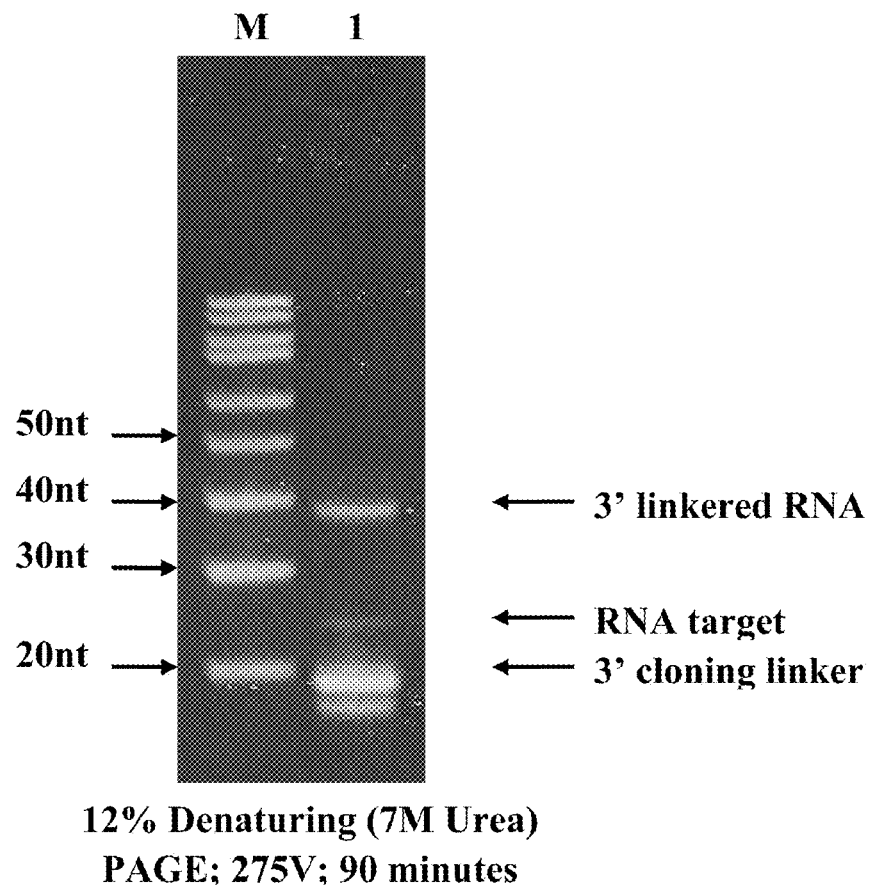
FIG. 6 is a 12% denaturing PAGE containing 3' linkered RNA. Marker (M) is an oligonucleotide length standard (Integrated DNA Technologies). Lane 1 shows the linkered RNAs at 40 nt.

The 3'-linkering reaction was run on a 12% denaturing PAGE, stained, and products visualized under UV excitation. The miSPIKE ORN marker now migrated around 40 nt size (due to the addition of the 3'-linker). RNAs co-migrating with the ligated marker were excised from the gel (see FIG. 6). Linkered RNAs were recovered from the gel slices as previously described.

5' Linkering reaction. The 5' multiple restriction site (M.R.S.) linker was ligated to the small RNAs recovered from gel purification above, this time using T4 RNA Ligase in the presence of 1.0 mM ATP. The M.R.S. linker contains five restriction sites and is therefore compatible with the Ban I 3'-linker employed in earlier steps. Sequence of the M.R.S. linker employed is shown below.

```
                                              SEQ ID NO: 10
5' TGGAATrUrCrUrCrGrGrCrArCrCrArArGrGrU 3'
```

The following was added to an RNase-free 0.2 ml tube:

| Recovered 3' linkered RNA fraction | 6 µl |
| 5' RNA linker (50 µM) | 1 µl |
| 10X Ligation Buffer | 2 µl |
| DMSO | 6 µl |
| 10 mM ATP | 2 µl |
| T4 RNA Ligase (5 U/µl) | 1 µl |
| Nuclease-free water | 2 µl |
| Total Volume | 20 µl |

The ligation reactions were incubated at 22° C. for two hours. Following incubation, 80 µl TE (pH 7.5) was added and the entire volume transferred to an RNase-free 1.5 ml tube. 3 µl glycogen (10 mg/ml), 1/10 volume (10 µl) 3.0 M NaOAc and 2.5 volumes (250 µl) −20° C. 100% EtOH was added, mixed, and stored at −80° C. for 30 min. The sample was centrifuged at 16000×g for 10 min. and the supernatant removed. The pellet was dried and resuspended in 10 µl nuclease-free water.

Reverse Transcription. At this point the 5' and 3' ligated RNAs contain both RNA and DNA regions. These are converted to DNA via reverse transcription using a RT/REV primer. For this example, the cDNA reverse transcripts have Ban I restriction sites at both ends that were designed into the linkers. The following RT primer was employed:

```
5'-GATTGATGGTGCCTACAG-3'       SEQ ID NO: 3
```

Reverse transcription was performed in the following reaction mix in a 0.2 ml tube.

| Recovered linkered RNA fraction | 10 µl |
| dNTPs (10 mM) | 1.0 µl |
| RT primer (10 µM) | 1.0 µl |
| DNase/RNase/pyrogen-free water | 1.0 µl |
| Total Volume | 13.0 µl |

The sample was incubated at 65° C. for 5 minutes, placed on ice, and then 4 µl 5× First Strand Buffer, 1 µl 0.1 M DTT, 1 µl RNase-OUT™ (40 U/µl), and 1 µl SuperScript™ III RT (200 U/µl) were added for a total volume of 20 µl. The sample was incubated at 50° C. for one hour followed by a 15 minute incubation at 70° C.

Figure 7:
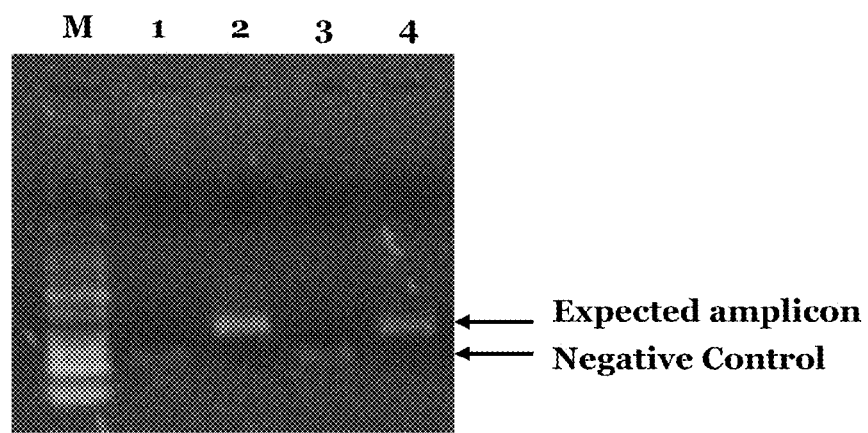
FIG. 7 is a 1.4% Low Melting Point Agarose gel containing replicate PCR reactions. The marker (M) is the Low Molecular Weight Marker from New England Biolabs. Lanes 1 and 3 are negative control reactions. Lanes 2 and 4 show the expected PCR amplicons.
Figure 8:
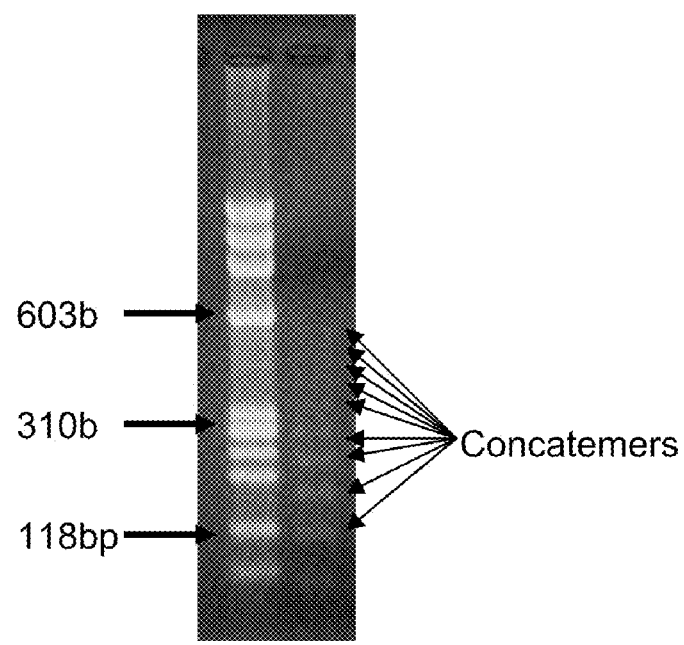
FIG. 8 shows a gel photograph of a Ban I concatamerization on a 1.4% Low Melting Point Agarose Gel. The concatamers continue beyond 600 bp (ten concatamers) but the very low mass of these products makes them difficult to see on the photograph.
Figure 9:
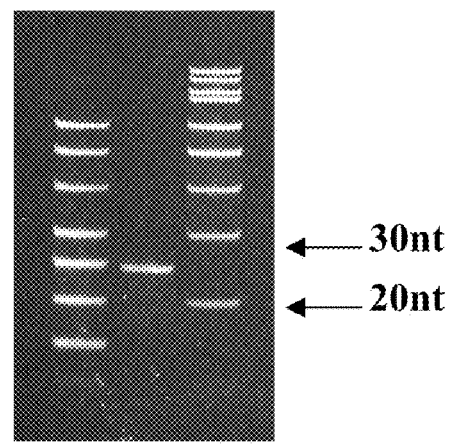
FIG. 9 shows a gel photograph of a mir-21 RNA (22-mer) with a 5' phosphate group (R) run on a 15% denaturing PAGE for 90 minutes at 275V. The markers are IDT Oligo Ladders 10-60 (left) and 20-100 (right).

PCR and Cloning. Standard PCR amplifications of the reverse transcribed linkered RNAs yielded expected amplicons (see FIG. 7). SEQ ID NO:4 served as the Forward PCR primer and SEQ ID NO: 3 served as the Reverse PCR primer. PCR amplification conditions consisted of a single initial incubation at 95° C. for five minutes followed by 25 cycles of 95° C. for 30 seconds, 52° C. for 30 seconds, and 72° C. for 30 seconds. A final extension incubation at 72° C. for five minutes followed the cycling to ensure that all PCR amplicons were full length.

Concatamers. PCR amplicons were digested with the restriction endonuclease Ban I and concatamerized by ligation using 30U of T4 DNA Ligase (Epicentre Biotechnologies). The result of this process is shown in FIG. 10.

Concatemer Cloning. Concatemers were cloned into the pGEM T-EASY cloning vector following manufacturer's (Promega) protocol.

Concatemer Sequencing. 480 bacterial colonies containing concatamer clones were directly sequenced on an Applied Biosystems Model 3130×1 Genetic Analyzer. From these sequences, more than 100 unique sequence signatures in the expected size range of 21 nt to 24 nt were identified. Of these, 92 were confirmed in miRBase as previously identified mammalian microRNAs. Identification of these previously known miRNA sequences validates the performance of the method and also confirms their existence and expression in *Monodelphis*. An additional fifteen sequences were subsequently validated as new, marsupial-specific microRNAs. These sequences are shown below.

TABLE 1

Sequences and miRBase assignments of fifteen new marsupial microRNAs.

| SEQ ID NO: | Sequence ID | miRBase # | Cloned RNA sequence |
|---|---|---|---|
| 13 | Mdo-10 | mdo-miR-1540 | UGAUUCCAUAGAGCGCAUGU |
| 14 | Mdo-27# | mdo-miR-1541 | UGGUGUGCUCGUUUGGAUGUGG |
| 15 | Mdo-172a | mdo-miR-1542-1 | UAUUGAUCUCCAAUGCCUAGC |
| 16 | Mdo-172b | mdo-miR-1542-2 | UAUUGAUCUCCAAUGCCUAGC |
| 17 | Mdo-174 | mdo-miR-1543 | UUAGUCCUAGUCUAGGUGCACA |
| 18 | Mdo-182 | mdo-miR-340 | AAGUAAUGAGAUUGAUUUCUGU |
| 19 | Mdo-202# | mdo-miR-1545 | UGCACCCAGGGAUAGGAUAGCG |
| 20 | Mdo-253-3p# | mdo-miR-1544-3p | ACUUUCCAUCCCUUGCACUGU |
| 21 | Mdo-253-5p# | mdo-miR-1544-5p | AGUGUCCUGGGAUAGAUAGGCG |
| 22 | Mdo-254 | mdo-miR-1546 | UCAGGGAUUCUCAGGGAUGGAA |
| 23 | Mdo-302 | mdo-miR-1547 | UAUCAGAGUCUUGGGUCCUUGU |
| 24 | Mdo-305 | unassigned* | UGCAUCCUGCAGCGGGCUCCCC |
| 25 | Mdo-315 | unassigned* | UUCCGCCCUGCAAGCCCGGUA |
| 26 | Mdo-204 | unassigned* | GUAACAGCCCACGAUGGUUUG |
| 27 | Mdo-301 | unassigned* | CCGCUCCGCUUGGUGCUGGCG | microRNA found in *Monodelphis domestica* only. All other miRNAs validated in additional marsupial species.
*microRNA has not been assigned a miRBase ID number as of Release 11.0 (April 2008).

Example 3

The following example demonstrates the use of the method of the invention to isolate novel piRNAs from tissue.

Unlike miRNAs which are expressed in all tissues, other classes of small RNAs have limited tissue distribution. The Piwi associated RNAs (piRNAs) are a different class of small RNA which are specific to gonads (ovary and testis). The piRNAs are longer than miRNAs, and usually are 26-32 nt long. The method of the invention was used to isolate and sequence identify novel piRNAs. Total RNA was prepared from testis of the South American marsupial species *Monodelphis domestica* using the MIRVANA™ RNA isolation kit (Ambion®, Austin, TX.) according to the manufacturer's protocol. Between 100 µg and 200 µg of total cellular RNA was obtained from each tissue fragment. 100 µg testis derived RNA was employed for the experiment. This RNA sample was spiked with 10 pmole of the 31 nt internal control ORN marker "piSPIKE" and size fractionated on a 12% denaturing (7M urea) polyacrylamide gel at 275 volts for 90 minutes.

```
                                              SEQ ID NO: 2
5'-rCrUrCrArGrGrArUrGrGrCrGrGrArGrCrGrGrUrCrUrCrAr
CrUrGrArArCrGrU-3'
```

The gel was stained with GelStar® and RNAs were visualized under UV excitation. A 4 mm square gel slice was excised using the miSPIKE ORN marker as a size guide. The gel slice was cut 2 mm above the ORN marker and 2 mm below the marker, thereby recovering RNAs in ~26-34 nt size range. The gel slice was pulverized in 200 µl of sterile, RNase-free water in a 1.5 ml microcentrifuge tube. The pulverized slurry was heated at 70° C. for 10 minutes and the entire volume was loaded on an EDGE Biosystems Performa® spin column and centrifuged for 3 minutes at 3,000 rpm. The target RNAs passed through the column and were recovered in the eluent while the acrylamide, salts and urea were retained within the column. The RNAs were precipitated with the addition of 3 µl of 10 mg/ml glycogen, 25 µl of 3M sodium acetate (pH 5.2), and 900 µl of cold 100% ethanol. The precipitated RNA was centrifuged for 10 minutes at 13,500 rpm to pellet the RNAs and was dried under vacuum.

3' small RNA linkering. The target RNAs were ligated to the adenylated 3' cloning linker Ban I (Linker 1 and SEQ ID NO:3) using the protocol in Example 1. In order to avoid circularization of the small RNAs, the 3' linker is ligated to the small RNAs using T4 RNA Ligase in the absence of ATP. This reaction involves a pre-activated 5' adenylated (rApp) cloning linker with a 3' ddC end-block (Lau et al., 2001).

In an RNase-free 0.2 ml tube the following reagents were added:

| | |
|---|---|
| Recovered small RNA fraction | 6 µl |
| 3' RNA linker (50 µM) | 1 µl |
| 10X Ligation Buffer | 2 µl |
| DMSO | 6 µl |
| T4 RNA Ligase (1 U/µl) | 1 µl |
| Nuclease-free water | 4 µl |
| Total Volume | 20 µl |

The 10× Ligation Buffer employed was the buffer provided by Epicentre Technologies with their T4 RNA Ligase. In this case, DMSO serves as a ligation enhancer which improves efficiency of the reaction. SEQ ID NO:3 is an adenylated cloning linker containing a Ban I restriction endonuclease site, which is underlined.

```
5'-rAppCTGTAGGCACCATCAAT/3ddC/-3'     SEQ ID NO: 9
```

The ligation reaction was incubated at 22° C. for two hours. Then 80 µl TE (pH 7.5) was added and the entire volume transferred to an RNase-free 1.5 ml tube. 3 µl glycogen (10 mg/ml), ¹/₁₀ volume (10 µl) 3.0 M NaOAc and 2.5 volumes (250 µl) 100% EtOH were added, mixed, then placed at −80° C. for 30 min. The sample was centrifuged at 16000×g for 10 min. The supernatant was removed, the pellet was dried and resuspended in 10 µl water.

The 3'-linkering reaction was run on a 12% denaturing PAGE, stained, and products visualized under UV excitation. The piSPIKE ORN marker now migrated around 48 nt size (due to the addition of the 3'-linker). RNAs co-migrating with the ligated marker were excised from the gel (see FIGS. 6 and 7). Linkered RNAs were recovered from the gel slices as previously described.

5' Linkering reaction. The 5' multiple restriction site (M.R.S.) linker was ligated to the small RNAs recovered from gel purification above, this time using T4 RNA Ligase in the presence of 1.0 mM ATP. The M.R.S. linker contains five restriction sites and is therefore compatible with the Ban I 3'-linker employed in earlier steps. Sequence of the M.R.S. linker employed is shown below.

```
                                             SEQ ID NO: 10
5'  TGGAATrUrCrUrCrGrGrGrCrArCrCrArArGrGrU 3'
```

The following was added to an RNase-free 0.2 ml tube:

| | |
|---|---|
| Recovered 3' linkered RNA fraction | 6 µl |
| 5' RNA linker (50 µM) | 1 µl |
| 10X Ligation Buffer | 2 µl |
| DMSO | 6 µl |
| 10 mM ATP | 2 µl |
| T4 RNA Ligase (5 U/µl) | 1 µl |
| Nuclease-free water | 2 µl |
| Total Volume | 20 µl |

The ligation reactions were incubated at 22° C. for two hours. Following incubation, 80 µl TE (pH 7.5) was added and the entire volume transferred to an RNase-free 1.5 ml tube. 3 µl glycogen (10 mg/ml), ¹/₁₀ volume (10 µl) 3.0 M NaOAc and 2.5 volumes (250 µl)-20° C. 100% EtOH was added, mixed, and stored at −80° C. for 30 min. The sample was centrifuged at 16000×g for 10 min. and the supernatant removed. The pellet was dried and resuspended in 10 µl nuclease-free water.

Reverse Transcription. At this point the 5' and 3' ligated RNAs contain both RNA and DNA regions. These are converted to DNA via reverse transcription using a RT/REV primer. For this example, the cDNA reverse transcripts have Ban I restriction sites at both ends that were designed into the linkers. The following RT primer was employed:

```
5'-GATTGATGGTGCCTACAG-3'     SEQ ID NO: 3
```

Reverse transcription was performed in the following reaction mix in a 0.2 ml tube.

| | |
|---|---|
| Recovered linkered RNA fraction | 10 µl |
| dNTPs (10 mM) | 1.0 µl |
| RT primer (10 µM) | 1.0 µl |
| DNase/RNase/pyrogen-free water | 1.0 µl |
| Total Volume | 13.0 µl |

The sample was incubated at 65° C. for 5 minutes, placed on ice, and then 4 µl 5× First Strand Buffer, 1 µl 0.1 M DTT, 1 µl RNase-OUT™ (40 U/µl), and 1 µl SuperScript™ III RT (200 U/µl) were added for a total volume of 20 µl. The sample was incubated at 50° C. for one hour followed by a 15 minute incubation at 70° C.

PCR and Cloning. Standard PCR amplifications of the reverse transcribed linkered RNAs yielded expected amplicons (see FIG. 7). SEQ ID NO:4 served as the Forward PCR primer and SEQ ID NO: 3 served as the Reverse PCR primer. PCR amplification conditions consisted of a single initial incubation at 95° C. for five minutes followed by 25 cycles of 95° C. for 30 seconds, 52° C. for 30 seconds, and 72° C. for 30 seconds. A final extension incubation at 72° C. for five minutes followed the cycling to ensure that all PCR amplicons were full length.

Concatamers. PCR amplicons were digested with the restriction endonuclease Ban I and concatamerized by ligation using 30U of T4 DNA Ligase (Epicentre Biotechnologies). The result of this process is shown in FIG. 10.

Concatamer Cloning. Concatamers were cloned into the pGEM T-EASY cloning vector following manufacturer's (Promega) protocol.

Concatamer Sequencing. 600 bacterial colonies containing concatamer clones were directly sequenced on an Applied Biosystems Model 3130x1 Genetic Analyzer. From these sequences, 406 unique sequence signatures were identified after identical cloned sequences were pooled. Of the 406 unique signatures, 310 (87.8%) were found to be in the expected size range of 28 nt to 31 nt. Analysis of these 310 sequences showed that they conform to the criteria accepted for identification of a new small RNA class called PIWI-interacting RNAs (piRNAs). These criteria include a length of 28 nt to 31 nt, a pronounced preference for a 5' uridine base (83.5% of these sequence signatures have a 5' U), transcription from large clusters (most of these sequences mapped to one of sixteen transcription clusters in the *M. domestica* genome), and targets of action that are primarily transposons (38 marsupial transposon targets were identified). Representative sequence identify are shown below.

TABLE 2 piRNA-like RNA sequences returning more than 100 full-length BLAST hits in the MonDom5 *M. domestica* genome assembly. Flanking sequence from MonDom5 was used to query each insert sequence in RepeatMasker to obtain a transposon identification. One sequence, MdopiR-263, was deleted from this group and reassigned as MdopiR-162 after further analysis.

| SEQ ID NO: | piRNA ID | Insert Sequence | Repeat Masker Transposon ID |
|---|---|---|---|
| 28 | MdopiR-245 | UCAUCUAUAAAAUUAGUCGGAGAAGGAAA | Mar1a Mdo |
| 29 | MdopiR-246 | UGGAUUUGGAAUCAGAGGAUGUGGGU | No ID |
| 30 | MdopiR-247 | UAGUGCCAAUAGAGCGUAAGGUCAAAGAGU | OposCharlie3a |
| 31 | MdopiR-247 | UAGUGCCAAUAGAGCGUAAGGUCAAAGAGU | LTR-ERV1 |
| 32 | MdopiR-248 | UUGAGGUAGUCUAUUUCAUUCGGUGCUGG | OposCharlie3a |
| 33 | MdopiR-250 | UGGGUCUGGAGUCAGGAAGCCUCAU | Mar1a Mdo |
| 34 | MdopiR-251 | GAGUCACUUAACCUGUUUGCCUCAGAUUCC | Mar1b Mdo |
| 35 | MdopiR-252 | AGUGGAUUGAGAGCCAGGCCUAGAGAUG | SINE1 Mdo |
| 36 | MdopiR-253 | UUGGCGAUUACAUUCCUGGGGGUUGU | L1 Mdo |
| 37 | MdopiR-254 | UCAGGUCAUGCAGAGAAAAGUCUAAUGGUCC | Mdo ERV2 |
| 38 | MdopiR-255 | UGUUGAAUGAAUGAAUGGAGGUUAUUUC | No ID |
| 39 | MdopiR-256 | CUUGAAUUCAAGACCUCCUGACUCUAGGCC | SINE1 Mdo |
| 40 | MdopiR-257 | UUUUGUGUCAUGGACCCCUUUGGUAGUCU | MIR3 MarsA |
| 41 | MdopiR-258 | UGCGGAUGACGUGUCCAGACCAUUGUAGC | RTE Mdo |
| 42 | MdopiR-259 | UGGUAUCCAUUUUCUACAAAACCCUGUUGC | Mdo ERV2 |
| 43 | MdopiR-260 | UCAUUUUAUGUAUGAGAAACUGAGAUAAA | Mar1a Mdo |
| 44 | MdopiR-261 | UGGGAUAUAAACUUGCCGGGACCAAUGCC | No ID |
| 45 | MdopiR-262 | UUCUAUGUUAACCACUCGGGGAUUAUUAGG | Mdo ERV15 |

TABLE 2-continued piRNA-like RNA sequences returning more than 100
full-length BLAST hits in the MonDom5 M. domestica
genome assembly. Flanking sequence from MonDom5
was used to query each insert sequence in RepeatMasker
to obtain a transposon identification. One sequence,
MdopiR-263, was deleted from this group and
reassigned as MdopiR-162 after further analysis.

| SEQ ID NO: | piRNA ID | Insert Sequence | Repeat Masker Transposon ID |
|---|---|---|---|
| 46 | MdopiR-264 | UGGAUUCAUAUCUGACCUCAGACACUUC | SINE1 Mdo |
| 47 | MdopiR-265 | GUUAAUAUUAAUUUGUACCCCUUUUAGGCCC | L1 Opos |
| 48 | MdopiR-266 | UGAUACAUACUAGCUGUGUAACCGUGGAC | Mar 1c Mdo |
| 49 | MdopiR-267 | GGAUUGAGAGCCAGGCCUAGAGAUAGGAGGUC | SINE1 Mdo |
| 50 | MdopiR-268 | AGUGGAAUGAGAACCAGGCCUAGAGAUG | SINE1 Mdo |
| 51 | MdopiR-269 | UGUAAAAUGAGAGAGUUGGUGUAGGUGGC | MIR3 MarsB |
| 52 | MdopiR-270 | UUAUUUUAUAGAUAAGGAAACUGAGGCU | Tigger 3 |
| 53 | MdopiR-271 | UGUGAUUGGUAGAUAUAAGGACUUGGGGGU | LTR1k Mdo |
| 54 | MdopiR-272 | UGGACUGAGAGCCAGGCCUAGAGACUGGAGU | SINE1 Mdo |
| 55 | MdopiR-273 | UCAUGAGUCCCUUGGAGUUGUCUUGGGU | L1 Opos |
| 56 | MdopiR-274 | GCAUUGGUGGUUCAGUGGUAGAAUUCUCG | tRNA-GLY |
| 57 | MdopiR-275 | UUGUGGAUAAUUUCCAUUUUGGGAGGCA | L1 Mdo |
| 58 | MdopiR-276 | UGAUGAUGUUUGAGCAGGGAUGGACAGA | LTR2e MD |
| 59 | MdopiR-277 | UGCUUUGUUUCUUCUCAGGCUGGUCAC | LTR106 MD |
| 60 | MdopiR-278 | UUGCAGCCAUAUUAACCCGGAAGUCCGCUC | L1 Mdo |
| 61 | MdopiR-279 | UUAAAAAAAAAUACUGGUGUAGA | L1 Mdo |
| 62 | MdopiR-280 | UACACAGCCAGUUAGUGUCUGAGGCCACAAAA | Mar1a Mdo |
| 63 | MdopiR-281 | UGGCAAACCUUUUAGAGACAGAGUGCCCA | OposCharlie3a |

Example 4

Figure 11:
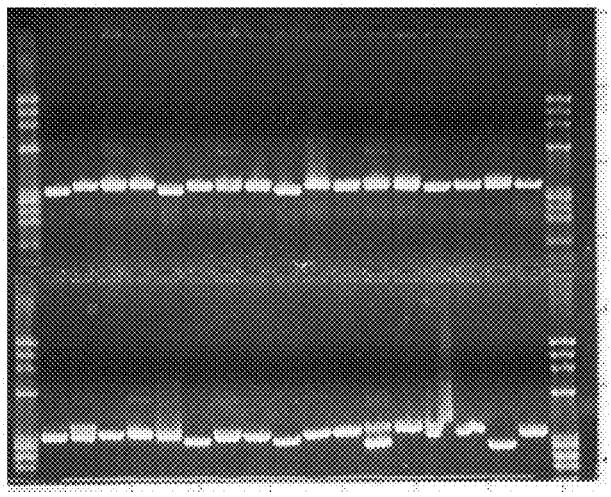
FIG. 11 is a photograph of colony PCR reactions run on a 1.4% Low Melting Point Agarose gel. The amplicons on the top are from the PCR reaction on the left in FIG. 8 while those on the bottom are from the PCR reaction on the right in FIG. 12.

The following example demonstrates the recovery of small RNA fractions in an RNA sample. Accurate recovery of the small RNA fraction as well as the 3' linkered RNAs from that fraction under conventional methods is difficult. To illustrate the dilemma, a 22-mer RNA with a 5' phosphate group was run on a 15% denaturing acrylamide gel adjacent to an Oligo Size Ladder (Integrated DNA Technologies). The result, shown in FIG. 11, is that the RNA runs high compared to the Size Ladder that is composed of single-stranded DNAs. The following example demonstrates the improvement of fraction collection utilizing an internal marker.

SEQ ID NO: 1 was synthesized without a 5' phosphate. Two samples were kept separate throughout the process. One of the two samples was purified via the "crush and soak", NAP column method after both denaturing PAGE gels. The other sample was purified after each of the two denaturing PAGE gels by pulverizing the acrylamide gel slice in 200 µl of IDT water and vortexing until the gel became a slurry in the tube. This slurry was then transferred to a DTR column (Edge Biosystems) and centrifuged for three minutes at 3000 rpm as per the manufacturers' instructions. The eluent was precipitated in 1/10 volume of NaOAc (pH 8.0) and three volume of ice cold ethanol with glycogen as the co-precipitant. The precipitant was dried down and both the crush and soak sample and the DTR column sample were used in each subsequent step as per the miRNA cloning kit protocol. FIG. 10A shows a comparison of total cotton RNA with and without 10 pmole of the 21-mer spiked into the reaction. FIG. 10B shows the linkering control function as the 3' linkered (with 454 3' linker) material is clearly visible and serves as an internal size marker for RNA recovery at that step as well (b). The recovered linkered material in FIG. 10B was 5' linked with the 454 5' sequence and then carried through an RT-PCR. The PCR gel is shown in FIG. 10C.

The two PCRs from lanes 2 and 3 of FIG. 10B were cloned separately into pGEM T-EASY and seventeen clones from each reaction were amplified with M13 For and M13 Rev. The Colony PCR gel is shown in FIG. 11. As can be seen, with only a couple of exceptions the colony PCRs in FIG. 11 compare favorably with those in FIG. 7.

Given the mass difference between the target small RNA fraction and the 10 pmole of control RNA spiked in, it is evident that the lack of the 5' phosphate on the control 21-mer RNA successfully prevented participation in any enzymatic steps following recovery of the 3' linkered species. None of the sequences from the 34 clones contained the 21-mer RNA control sequence. Moreover, the breakdown of the 34 sequences was better than previously seen in cotton RNAs. Of the 34 clone sequences, only one did not have an insert (3%), ten were linker-linker clones (29%), and the remaining 23 clones were all linker-RNA-linker. Among these was a definite microRNA (miR-167), 14 unidentified RNAs, and eight identified RNA including two sequences identical to so-called "small RNAs" from *Arabidopsis thaliana* (Qi et al. (2006) Nature 443: 1008-1012), two cotton sequences, of which one is a microsatellite, a fragment of the OGRE retrotransposon previously identified only in *Pisum sativum* (Neumann et al. (2003) *Plant Molecular Biology* 53: 399-410), and a fragment of an RNA binding protein gene sequence.

The quality and content of these 34 clones appears to be better than those previously obtained without the spiked in 21-mer RNA, which may mean that the 21-mer is serving as a carrier.

The colony PCRs in FIG. 11 are from the two treatments with the crush and soak material on the top and the DTR column material on the bottom. The clone sequences from the two sets displayed no difference. The results demonstrate that the DTR column method can replace the crush and soak, thereby eliminating time and effort (essentially one full day) from the preparation. The two crush and soaks required very long dry downs owing to the elution volume of 1.0 ml from the NAP-5 columns. The DTR column procedure took one hour.

Example 5

Oligonucleotide Adenylation Using Diphenyl Phosphate

Figure 12:
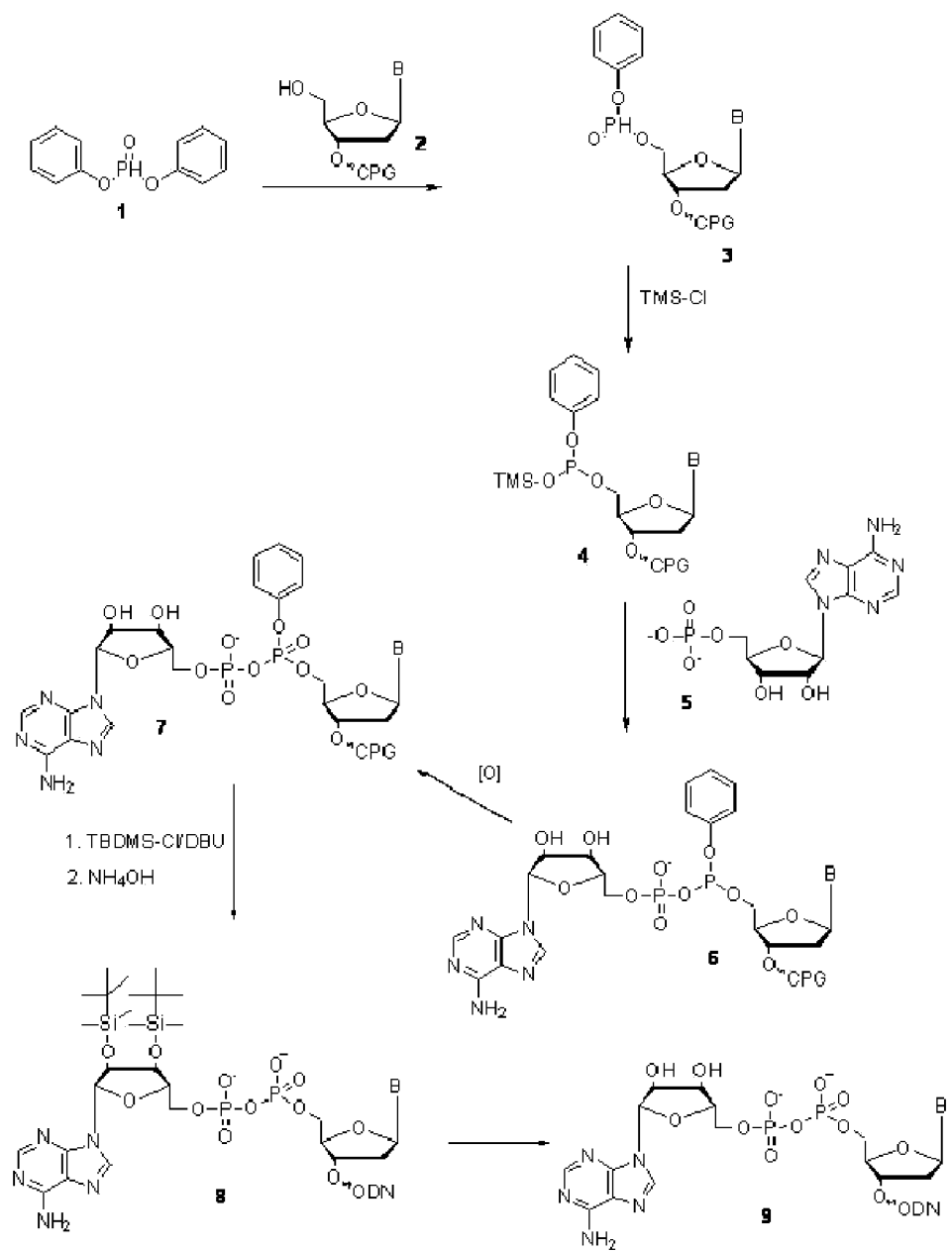
FIG. 12 is a schematic illustration of the synthesis of an on-support adenylation of an oligonucleotide using diphenyl phosphate.

The following example demonstrates the on-support adenylation of an oligonucleotide using diphenyl phosphate. The reference numbers correspond to the synthesis scheme in FIG. 12.

Solid support-bound oligonucleotide having a free 5' hydroxyl group (2) was phosphitylated with 0.5 M diphenyl phosphate (1) in a 50%/35%/15% (v/v) acetonitrile/pyridine/ N-methylimidazole solution for five minutes. The solid support was rinsed with 1 mL of 1:1 pyridine/acetonitrile. The phosphitylated oligonucleotide was converted to a phosphite triester (3) with chlorotrimethylsilane (10% in pyridine) and immediately treated with a 40 molar excess of adenosine monophosphate (4) in a 70/30 pyridine/N-methylimidazole solution for 30 minutes. After rinsing the column with 1:1 pyridine/acetonitrile, the adenylated oligonucleotide was oxidized with 0.1 M N-chlorosuccinimide in pyridine for 20 minutes. After oxidation and rinsing with 1:1 pyridine/acetonitrile, the unprotected ribose was labeled with tert-butyldimethylsilyl chloride (1 M in acetonitrile with 10% 1,8-Diazabicyclo[5.4.0]undec-7-ene) for 15 minutes. The column was rinsed with acetonitrile to remove excess TBDMS chloride. The adenylated oligonucleotide was cleaved and deprotected in ammonia for one hour at 65° C. The oligonucleotide (8) was purified by RP HPLC. After lyophilization, the two silyl groups were removed from the oligonucleotide 8 with a 30 minute treatment of 5% tetraethylammonium fluoride in DMSO. The molecular weight of the final oligonucleotide (9) was verified by ESI mass-spectrum.

Example 6

Oligonucleotide Adenylation Using Salicyl Chlorophosphite

Figure 13:
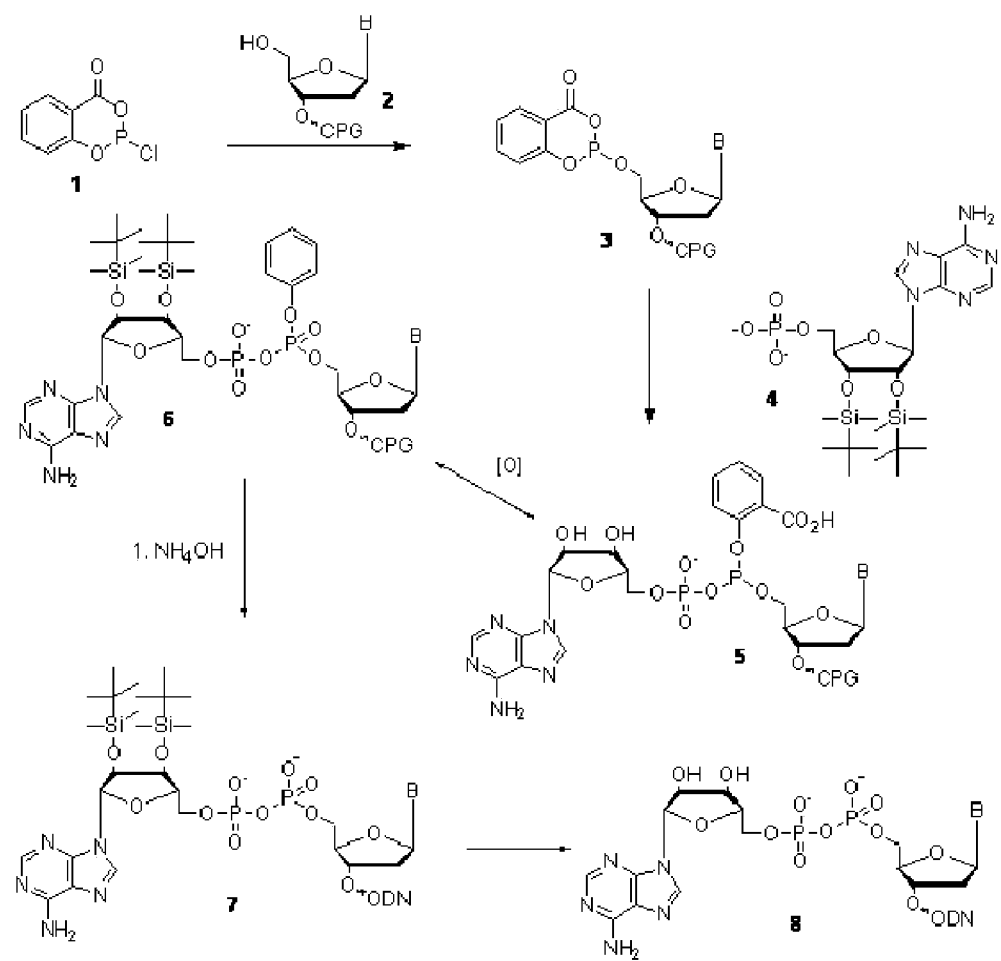
FIG. 13 is a schematic illustration of the synthesis of an on-support adenylation of an oligonucleotide using salicyl chlorophosphite.

The following example demonstrates an alternative on-support adenylation of an oligonucleotide using salicyl chlorophosphite. The reference numbers correspond to the synthesis scheme in FIG. 13.

Solid support-bound oligonucleotide (2) was phosphitylated 2×15 minutes with a solution of 0.1 M salicyl chlorophosphite (1) in acetonitrile pre-wetted with pyridine. The oligonucleotide was immediately treated with a 40 molar excess of bis-TBDMS-adenosine monophosphate (4) in a 70/30 pyridine/N-methylimidazole solution for 30 minutes. After rinsing the solid support with 1:1 pyridine/acetonitrile, the phosphite triester (5) was oxidized with 0.1 M N-chlorosuccinimide in pyridine for 20 minutes. The oligonucleotide was rinsed with 1:1 pyridine/acetonitrile and cleaved and deprotected in ammonia for one hour at 65° C. After lyophilization and RP HPLC purification, the desired oligonucleotide 7 was verified by ESI. The silyl groups were removed with 5% tetraethylammonium fluoride in DMSO for 30 minutes. The molecular weight of final oligonucleotide (8) was confirmed by ESI mass-spectrum.

Example 7

5' Ligation-Independent Cloning

The following example provides an alternative method for cloning small RNA species with 5' modifications that render them refractory to conventional cloning. In conventional small RNA cloning, including the methods in prior examples, cloning begins with enrichment of the small RNA fraction of total RNA followed in order by a 3' ligation of a linker sequence, a 5' ligation of a second linker sequence, reverse transcription, PCR amplification and cloning. The success of these methods relies on the fact that the small RNAs will have a 3' hydroxyl group and a 5' phosphate group. Recently, Pak and Fire (*Science* 315: 241-244 (2007)) showed that some small RNA species in *C. elegans* are tri-phosphorylated on the 5' end and, therefore, cannot be cloned by conventional methods. This raises the possibility that there are other small RNAs with 5' modifications that render them refractory to conventional cloning.

Pak and Fire (2007) introduced a modification of the conventional small RNA cloning procedure that circumvents the problem of non-standard 5' ends. Called "5' ligation-independent cloning", this modification involves reversing two of the steps in the conventional protocol. Following 3' ligation, the ligated material is reverse transcribed and then a second 3' ligation is carried out using a different linker sequence.

The following oligonucleotides can be used in a 5' ligation-independent cloning protocol.

5'-rAppTGGAATTCTCG<u>GGTGCC</u>AAGGT/ddC/-3'  SEQ ID NO: 64

5'-CCTT<u>GGCACC</u>CGAGAATT-3'  SEQ ID NO: 65

Reverse transcription reaction. The 3' ligated small RNA fragments contain both RNA and DNA regions. This is converted to an all DNA substrate via reverse transcription using the RT/REV primer, which presents a free 3' hydroxyl group that could be used in a second ligation reaction. The reverse transcription protocol provided below is for SuperScript™ III Reverse Transcriptase (Invitrogen Cat. Nos. 18080-093 or 18080-044). The following are added to an RNase-free 0.2 ml tube:

| | |
|---|---|
| Recovered linkered RNA fraction | y µl |
| dNTPs (10 mM) | 1.0 µl |
| RT primer (10 µM) | 1.0 µl |
| nuclease/pyrogen-free water | (11.0 − y) µl |
| Total Volume | 13.0 ul |

This is incubated at 65° C. for 5 minutes and then the following are added:

| | |
|---|---|
| 5X First Strand Buffer | 4 µl |
| 0.1 M DTT | 1 µl |
| RNase-OUT ™ (40 U/µl) | 1 µl |
| SuperScript ™ III RT (200 U/µl) | 1 µl |
| Total Volume | 20.0 µl |

This is incubated at 50° C. for one hour followed by a 15 minute incubation at 70° C.

Exonuclease digest. An exonuclease digest is carried out to remove the unused deoxynucleotides and the primer. The protocol is for the ExoSAP-IT® (USB Cat. No. 78200) clean up. ExoSAP-IT® contains Exonuclease I and shrimp alkaline phosphatase in a buffer that is compatible with the RT reaction. Thus no buffer exchange or precipitation is required prior to performing the clean up.

20 µl of RT reaction is added to 8 µl of ExoSAP-IT® for a total volume of 28 µl. This is incubated for 15 minutes at 37° C. An equal volume of Phenol:Chloroform:Isoamyl Alcohol (25:24:1) is added, and then the solution is vortexed and centrifuged at 16000×g for 3 min. The aqueous (upper) phase is transferred to a new 0.2 ml tube and 2.8 µl of 3 M NaOAc is added. 90 µl of cold 100% EtOH is added and the tube is placed at −80° C. for 20 minutes. The sample is then centrifuged at 16000×g for 10 min and the supernatant is removed. The pellet is completely dried and resuspended in 10 µl nuclease/pyrogen-free water.

The second 3′ ligation. In an RNase-free 0.2 ml tube the following reagents are added:

| | |
|---|---|
| Resuspended Reverse Transcription Reaction | 10 µl |
| 3′ Linker-33 (50 µM) | 1 µl |
| 10X Ligation Buffer | 2 µl |
| DMSA | 6 µl |
| T4 RNA Ligase (1 U/µl) | 1 µl |
| Total Volume | 20 µl |

The above reagents are incubated at 22° C. for two hours and then 80 µl IDTE (pH 7.5) is added. The entire volume is transferred to an RNase-free 1.5 ml tube and 3 µl glycogen (10 mg/ml), 1/10 volume (10 µl) 3.0 M NaOAc, and 2.5 volumes (250 µl) −20° C. 100% EtOH are added. The sample is mixed by inversion or vortexed, and then placed at −80° C. for 30 min. The sample is then centrifuged at 16000×g for 10 min and the supernatant is removed. The pellet is completely dried and resuspended in 10 µl nuclease/pyrogen-free water.

PCR Amplification. After PAGE purification is performed (as in Example 1), the following reagents are combined for PCR:

| | |
|---|---|
| PAGE purified material | 3.0 µl |
| DNase/RNase/pyrogen-free water | 35.5 µl |
| 10x PCR Buffer | 5.0 µl |
| $MgCl_2$ (1.5 mM) | 3.0 µl |
| dNTPs (10 mM) | 1.0 µl |
| RT Primer (10 pmole) | 1.0 µl |
| REV-33 Primer (10 pmole) | 1.0 µl |
| Taq polymerase (5 U/µl) | 0.5 µl |
| Total Volume | 50.0 µl |

PCR is carried out as in Example 1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition for ensuring the selection of a desired fraction of RNA corresponding to microRNA during RNA purification, said composition comprising an artificial sequence SEQ ID NO:1.

2. A composition for ensuring the selection of a desired fraction of RNA corresponding to PIWI-interacting RNA during RNA purification, said composition comprising an artificial sequence SEQ ID NO:2.

* * * * *

SEQUENCE LISTING

<160> NUMBER OF SEQ ID NOS: 65

<210> SEQ ID NO 1
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 1
cucaggaugg cggagcgguc u                                              21

<210> SEQ ID NO 2
<211> LENGTH: 31
<212> TYPE: RNA
<213> ORGANISM: Artificial
<220> FEATURE:
<223> OTHER INFORMATION: Synthetic oligonucleotide

<400> SEQUENCE: 2
cucaggaugg cggagcgguc ucacugaacg u                                   31

<210> SEQ ID NO 3
<211> LENGTH: 18
<212> TYPE: DNA
<213> ORGANISM: Artificial
<220> FEATURE:
<223> OTHER INFORMATION: Synthetic oligonucleotide

<400> SEQUENCE: 3
gattgatggt gcctacag                                                  18

<210> SEQ ID NO 4
<211> LENGTH: 17
<212> TYPE: DNA
<213> ORGANISM: Artificial
<220> FEATURE:
<223> OTHER INFORMATION: Synthetic oligonucleotide

<400> SEQUENCE: 4
tggaattctc gggcacc                                                   17

<210> SEQ ID NO 5
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: biotin_label
<222> LOCATION: (1)..(1)

<400> SEQUENCE: 5
gattgatggt gcctacag                                                  18

<210> SEQ ID NO 6
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: biotin_label
<222> LOCATION: (1)..(1)

<400> SEQUENCE: 6
tggaattctg ggcacc                                                        16

<210> SEQ ID NO 7
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: biotin_label
<222> LOCATION: (2)..(2)

<400> SEQUENCE: 7
ctgattgatg gtgcctacag                                                    20

<210> SEQ ID NO 8
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: biotin_label
<222> LOCATION: (2)..(2)

<400> SEQUENCE: 8
cttggaattc tgggcacc                                                      18

<210> SEQ ID NO 9
<211> LENGTH: 19
<212> TYPE: DNA
<213> ORGANISM: Artificial
<220> FEATURE:
<223> OTHER INFORMATION: Synthetic oligonucleotide
<220> FEATURE:
<221> NAME/KEY: adenylated_allele
<222> LOCATION: (1)..(1)
<220> FEATURE:
<221> NAME/KEY: dideoxy-C
<222> LOCATION: (19)..(19)

<400> SEQUENCE: 9
actgtaggca ccatcaatc                                                     19

<210> SEQ ID NO 10
<211> LENGTH: 22
<212> TYPE: DNA
<213> ORGANISM: Artificial
<220> FEATURE:
<223> OTHER INFORMATION: Synthetic oligonucleotide

<400> SEQUENCE: 10
tggaatucuc gggcaccaag gu                                                 22

<210> SEQ ID NO 11
<211> LENGTH: 16
<212> TYPE: DNA
<213> ORGANISM: Artificial
<220> FEATURE:
<223> OTHER INFORMATION: Synthetic oligonucleotide

<400> SEQUENCE: 11
ctgtaggcac caaggt                                                        16

<210> SEQ ID NO 12
<211> LENGTH: 16
<212> TYPE: DNA
<213> ORGANISM: Artificial
<220> FEATURE:

```
<223> OTHER INFORMATION: Synthetic oligonucleotide

<400> SEQUENCE: 12
accttggtgc ctacag                                                    16

<210> SEQ ID NO 13
<211> LENGTH: 20
<212> TYPE: RNA
<213> ORGANISM: monodelphis domestica

<400> SEQUENCE: 13
ugauuccaua gagcgcaugu                                                20

<210> SEQ ID NO 14
<211> LENGTH: 22
<212> TYPE: RNA
<213> ORGANISM: monodelphis domestica

<400> SEQUENCE: 14
uggugugcuc guuuggaugu gg                                             22

<210> SEQ ID NO 15
<211> LENGTH: 21
<212> TYPE: RNA
<213> ORGANISM: monodelphis domestica

<400> SEQUENCE: 15
uauugaucuc caaugccuag c                                              21

<210> SEQ ID NO 16
<211> LENGTH: 21
<212> TYPE: RNA
<213> ORGANISM: monodelphis domestica

<400> SEQUENCE: 16
uauugaucuc caaugccuag c                                              21

<210> SEQ ID NO 17
<211> LENGTH: 22
<212> TYPE: RNA
<213> ORGANISM: monodelphis domestica

<400> SEQUENCE: 17 uuagccuag ucuaggugca ca                                              22

<210> SEQ ID NO 18
<211> LENGTH: 22
<212> TYPE: RNA
<213> ORGANISM: monodelphis domestica

<400> SEQUENCE: 18
aaguaaugag auugauuucu gu                                             22

<210> SEQ ID NO 19
<211> LENGTH: 22
<212> TYPE: RNA
<213> ORGANISM: monodelphis domestica

<400> SEQUENCE: 19
ugcacccagg gauaggauag cg                                             22

<210> SEQ ID NO 20
<211> LENGTH: 21
<212> TYPE: RNA
```

```
<213> ORGANISM: monodelphis domestica

<400> SEQUENCE: 20
acuuuccauc ccuugcacug u                                              21

<210> SEQ ID NO 21
<211> LENGTH: 22
<212> TYPE: RNA
<213> ORGANISM: monodelphis domestica

<400> SEQUENCE: 21
aguguccugg gauagauagg cg                                             22

<210> SEQ ID NO 22
<211> LENGTH: 22
<212> TYPE: RNA
<213> ORGANISM: monodelphis domestica

<400> SEQUENCE: 22
ucagggauuc ucagggaugg aa                                             22

<210> SEQ ID NO 23
<211> LENGTH: 22
<212> TYPE: RNA
<213> ORGANISM: monodelphis domestica

<400> SEQUENCE: 23
uaucagaguc uuggguccuu gu                                             22

<210> SEQ ID NO 24
<211> LENGTH: 22
<212> TYPE: RNA
<213> ORGANISM: monodelphis domestica

<400> SEQUENCE: 24
ugcauccugc agcgggcucc cc                                             22

<210> SEQ ID NO 25
<211> LENGTH: 20
<212> TYPE: RNA
<213> ORGANISM: monodelphis domestica

<400> SEQUENCE: 25
uuccgcccug caagcccggu                                                20

<210> SEQ ID NO 26
<211> LENGTH: 21
<212> TYPE: RNA
<213> ORGANISM: monodelphis domestica

<400> SEQUENCE: 26
guaacagccc acgauggnuu g                                              21

<210> SEQ ID NO 27
<211> LENGTH: 21
<212> TYPE: RNA
<213> ORGANISM: monodelphis domestica

<400> SEQUENCE: 27
ccgcuccgcu uggugcuggc g                                              21

<210> SEQ ID NO 28
<211> LENGTH: 29
<212> TYPE: RNA
```

<213> ORGANISM: monodelphis domestica

<400> SEQUENCE: 28
ucaucuauaa aauuagucgg agaaggaaa                                    29

<210> SEQ ID NO 29
<211> LENGTH: 26
<212> TYPE: RNA
<213> ORGANISM: monodelphis domestica

<400> SEQUENCE: 29
uggauuugga aucagaggau gugggu                                       26

<210> SEQ ID NO 30
<211> LENGTH: 30
<212> TYPE: RNA
<213> ORGANISM: monodelphis domestica

<400> SEQUENCE: 30
uagugccaau agagcguaag gucaaagagu                                   30

<210> SEQ ID NO 31
<211> LENGTH: 30
<212> TYPE: RNA
<213> ORGANISM: monodelphis domestica

<400> SEQUENCE: 31
uagugccaau agagcguaag gucaaagagu                                   30

<210> SEQ ID NO 32
<211> LENGTH: 29
<212> TYPE: RNA
<213> ORGANISM: monodelphis domestica

<400> SEQUENCE: 32
uugagguagu cuauuucauu cggugcugg                                    29

<210> SEQ ID NO 33
<211> LENGTH: 25
<212> TYPE: RNA
<213> ORGANISM: monodelphis domestica

<400> SEQUENCE: 33
ugggucugga gucaggaagc cucau                                        25

<210> SEQ ID NO 34
<211> LENGTH: 30
<212> TYPE: RNA
<213> ORGANISM: monodelphis domestica

<400> SEQUENCE: 34
gagucacuua accuguuugc cucagauucc                                   30

<210> SEQ ID NO 35
<211> LENGTH: 28
<212> TYPE: RNA
<213> ORGANISM: monodelphis domestica

<400> SEQUENCE: 35
aguggauuga gagccaggcc uagagaug                                     28

<210> SEQ ID NO 36
<211> LENGTH: 27
<212> TYPE: RNA

```
<213> ORGANISM: monodelphis domestica

<400> SEQUENCE: 36
uuggcgauua cauuccuggg ggguugu                                    27

<210> SEQ ID NO 37
<211> LENGTH: 31
<212> TYPE: RNA
<213> ORGANISM: monodelphis domestica

<400> SEQUENCE: 37
ucaggucaug cagagaaaag ucuaaugguc c                               31

<210> SEQ ID NO 38
<211> LENGTH: 28
<212> TYPE: RNA
<213> ORGANISM: monodelphis domestica

<400> SEQUENCE: 38
uguugaauga augaauggag guuauuuc                                   28

<210> SEQ ID NO 39
<211> LENGTH: 30
<212> TYPE: RNA
<213> ORGANISM: monodelphis domestica

<400> SEQUENCE: 39
cuugaauuca agaccuccug acucuaggcc                                 30

<210> SEQ ID NO 40
<211> LENGTH: 29
<212> TYPE: RNA
<213> ORGANISM: monodelphis domestica

<400> SEQUENCE: 40
uuuuguguca uggaccccuu ugguagucu                                  29

<210> SEQ ID NO 41
<211> LENGTH: 29
<212> TYPE: RNA
<213> ORGANISM: monodelphis domestica

<400> SEQUENCE: 41
ugcggaugac guguccagac cauuguagc                                  29

<210> SEQ ID NO 42
<211> LENGTH: 30
<212> TYPE: RNA
<213> ORGANISM: monodelphis domestica

<400> SEQUENCE: 42
ugguauccau uuucuacaaa acccuguugc                                 30

<210> SEQ ID NO 43
<211> LENGTH: 29
<212> TYPE: RNA
<213> ORGANISM: monodelphis domestica

<400> SEQUENCE: 43
ucauuuuaug uaugagaaac ugagauaaa                                  29

<210> SEQ ID NO 44
<211> LENGTH: 29
<212> TYPE: RNA
```

```
<213> ORGANISM: monodelphis domestica

<400> SEQUENCE: 44
ugggauauaa acugccggg accaaugcc                                              29

<210> SEQ ID NO 45
<211> LENGTH: 30
<212> TYPE: RNA
<213> ORGANISM: monodelphis domestica

<400> SEQUENCE: 45
uucuauguua accacucggg gauuauuagg                                            30

<210> SEQ ID NO 46
<211> LENGTH: 28
<212> TYPE: RNA
<213> ORGANISM: monodelphis domestica

<400> SEQUENCE: 46
uggauucaua ucugaccuca gacacuuc                                              28

<210> SEQ ID NO 47
<211> LENGTH: 31
<212> TYPE: RNA
<213> ORGANISM: monodelphis domestica

<400> SEQUENCE: 47
guuaauauua auuuguaccc cuuuuaggcc c                                          31

<210> SEQ ID NO 48
<211> LENGTH: 29
<212> TYPE: RNA
<213> ORGANISM: monodelphis domestica

<400> SEQUENCE: 48
ugauacauac uagcugugua accguggac                                             29

<210> SEQ ID NO 49
<211> LENGTH: 32
<212> TYPE: RNA
<213> ORGANISM: monodelphis domestica

<400> SEQUENCE: 49
ggauugagag ccaggccuag agauaggagg uc                                         32

<210> SEQ ID NO 50
<211> LENGTH: 28
<212> TYPE: RNA
<213> ORGANISM: monodelphis domestica

<400> SEQUENCE: 50
aguggaauga gaaccaggcc uagagaug                                              28

<210> SEQ ID NO 51
<211> LENGTH: 29
<212> TYPE: RNA
<213> ORGANISM: monodelphis domestica

<400> SEQUENCE: 51
uguaaaauga gagaguuggu guagguggc                                             29

<210> SEQ ID NO 52
<211> LENGTH: 28
<212> TYPE: RNA
```

<213> ORGANISM: monodelphis domestica

<400> SEQUENCE: 52
uuauuuuaua gauaaggaaa cugaggcu                                28

<210> SEQ ID NO 53
<211> LENGTH: 30
<212> TYPE: RNA
<213> ORGANISM: monodelphis domestica

<400> SEQUENCE: 53
ugugauuggu agauauaagg acuuggggu                               30

<210> SEQ ID NO 54
<211> LENGTH: 31
<212> TYPE: RNA
<213> ORGANISM: monodelphis domestica

<400> SEQUENCE: 54
uggacugaga gccaggccua gagacuggag u                            31

<210> SEQ ID NO 55
<211> LENGTH: 28
<212> TYPE: RNA
<213> ORGANISM: monodelphis domestica

<400> SEQUENCE: 55
ucaugagucc cuuggaguug ucuugggu                                28

<210> SEQ ID NO 56
<211> LENGTH: 29
<212> TYPE: RNA
<213> ORGANISM: monodelphis domestica

<400> SEQUENCE: 56
gcauuggugg uucaguggua gaauucucg                               29

<210> SEQ ID NO 57
<211> LENGTH: 28
<212> TYPE: RNA
<213> ORGANISM: monodelphis domestica

<400> SEQUENCE: 57
uuguggauaa uuccauuuu gggaggca                                 28

<210> SEQ ID NO 58
<211> LENGTH: 28
<212> TYPE: RNA
<213> ORGANISM: monodelphis domestica

<400> SEQUENCE: 58
ugaugauguu ugagcaggga uggacaga                                28

<210> SEQ ID NO 59
<211> LENGTH: 27
<212> TYPE: RNA
<213> ORGANISM: monodelphis domestica

<400> SEQUENCE: 59
ugcuuuguuu cuucucaggc uggucac                                 27

<210> SEQ ID NO 60
<211> LENGTH: 30
<212> TYPE: RNA

-continued

```
<213> ORGANISM: monodelphis domestica

<400> SEQUENCE: 60
uugcagccau auuaacccgg aaguccgcuc                                    30

<210> SEQ ID NO 61
<211> LENGTH: 23
<212> TYPE: RNA
<213> ORGANISM: monodelphis domestica

<400> SEQUENCE: 61
uuaaaaaaaa auacuggugu aga                                           23

<210> SEQ ID NO 62
<211> LENGTH: 32
<212> TYPE: RNA
<213> ORGANISM: monodelphis domestica

<400> SEQUENCE: 62
uacacagcca guuagugucu gaggccacaa aa                                 32

<210> SEQ ID NO 63
<211> LENGTH: 29
<212> TYPE: RNA
<213> ORGANISM: monodelphis domestica

<400> SEQUENCE: 63
uggcaaaccu uuuagagaca gagugccca                                     29

<210> SEQ ID NO 64
<211> LENGTH: 24
<212> TYPE: DNA
<213> ORGANISM: Artificial
<220> FEATURE:
<223> OTHER INFORMATION: Synthetic oligonucleotide
<220> FEATURE:
<221> NAME/KEY: adenylated_linker
<222> LOCATION: (1)..(1)
<220> FEATURE:
<221> NAME/KEY: dideoxy-C
<222> LOCATION: (24)..(24)

<400> SEQUENCE: 64
atggaattct cgggtgccaa ggtc                                          24

<210> SEQ ID NO 65
<211> LENGTH: 18
<212> TYPE: DNA
<213> ORGANISM: Artificial
<220> FEATURE:
<223> OTHER INFORMATION: Synthetic oligonucleotide

<400> SEQUENCE: 65
ccttggcacc cgagaatt                                                 18
```